(12) United States Patent
Ouyang et al.

(10) Patent No.: US 7,638,291 B2
(45) Date of Patent: Dec. 29, 2009

(54) IMMUNOASSAYS FOR TOPIRAMATE

(75) Inventors: Anlong Ouyang, Indianapolis, IN (US); Lili Arabshahi, Carmel, IN (US)

(73) Assignee: Seradyn, Inc., Indianapolis, IN (US)

( * ) Notice: Subject to any disclaimer, the term of this patent is extended or adjusted under 35 U.S.C. 154(b) by 0 days.

(21) Appl. No.: 11/254,507

(22) Filed: Oct. 20, 2005

(65) Prior Publication Data

US 2006/0088885 A1 Apr. 27, 2006

Related U.S. Application Data

(60) Provisional application No. 60/621,770, filed on Oct. 25, 2004.

(51) Int. Cl.
| | |
|---|---|
| G01N 33/53 | (2006.01) |
| G01N 33/573 | (2006.01) |
| G01N 33/532 | (2006.01) |
| G01N 33/533 | (2006.01) |
| C07K 16/00 | (2006.01) |
| C07K 1/04 | (2006.01) |
| C07D 321/10 | (2006.01) |

(52) U.S. Cl. .................. 435/7.93; 435/7.1; 435/7.9; 436/533; 436/535; 436/544; 436/546; 436/815; 530/403; 530/406; 530/388.9; 530/389.8; 549/200

(58) Field of Classification Search .................. 435/7.1, 435/7.93, 7.9, 132; 436/533, 535, 544, 545, 436/546, 127, 815; 530/403, 406, 388.9, 530/389.8; 549/200

See application file for complete search history.

(56) References Cited

U.S. PATENT DOCUMENTS

| | | | |
|---|---|---|---|
| 4,492,762 A | 1/1985 | Wang et al. | |
| 4,593,089 A | 6/1986 | Wang et al. | |
| 4,668,640 A | 5/1987 | Wang et al. | |
| 4,708,929 A | 11/1987 | Henderson | |
| 4,751,190 A | 6/1988 | Chiapetta et al. | |
| 4,847,209 A | 7/1989 | Lewis et al. | |
| 5,120,653 A | 6/1992 | Henderson | |
| 5,571,728 A | 11/1996 | Kraus | |
| 5,604,091 A | 2/1997 | Henderson | |
| 5,643,734 A | 7/1997 | Henderson | |
| 5,798,083 A | 8/1998 | Massey et al. | |
| 5,834,206 A | 11/1998 | Neuenhofer et al. | |
| 5,952,187 A * | 9/1999 | Stenglein et al. | 435/7.93 |
| 6,248,597 B1 | 6/2001 | Eda et al. | |
| 6,448,091 B1 | 9/2002 | Massey et al. | |
| 6,514,770 B1 | 2/2003 | Sorin | |
| 6,699,840 B2 | 3/2004 | Almarsson et al. | |
| 7,060,725 B2 | 6/2006 | Abdel-Magid et al. | |
| 7,098,188 B2 | 8/2006 | Abdel-Magid et al. | |
| 7,157,589 B2 | 1/2007 | Berkner et al. | |

| | | |
|---|---|---|
| 2004/0258758 A1 | 12/2004 | Gustow et al. |

FOREIGN PATENT DOCUMENTS

| | | |
|---|---|---|
| WO | WO 2006/047204 | 5/2000 |
| WO | WO 2006/047450 | 5/2006 |

OTHER PUBLICATIONS

Faivre-Chauvet et al. Introduction of five potentially metabolizable linking groups between in-cyclohexyl EDTA derivatives and F(ab')2 fragments of anti-carcinoembryonic antigen antibody-II. Comparative pharmacokinetics and biodistribution in Human colorectal carcinoma-bearing nude mice. Nucl. Med. Biol 1993, vol. 20, No. 6, pp. 763-771.*

Christensen, Jakob, et al.; "Liquid Chromatography Tandem Mass Spectrometry Assay for Topiramate Analysis in Plasma and Cerebrospinal Fluid: Validation and Comparison with Fluorescence-Polarization Immunoassay," *Therapeutic Drug Monitoring*, 24:658-665; received Nov. 14, 2001; accepted Mar. 27, 2002.

Berry, David J., et al.; "Comparison of Topiramate Concentrations in Plasma and Serum by Fluorescence Polarization Immunoassay," *Therapeutic Drug Monitoring*, 22:460-464; received Aug. 2, 1999, accepted Feb. 29, 2000.

Chen, Su, et al.; "Validation of liquid-liquid extraction followed by flow-injection negative ion electrospray mass spectrometry assay to Topiramate in human plasma," *Rapid Communications in Mass Spectrometry*, 2001; 15:159;163.

Tang, Peter H., et al.; "An Improved Gas Chromatography Assay for Topiramate Monitoring in Pediatric Patients," *Therapeutic Drug Monitoring*, 22:195-201; received Feb. 23, 1999; accepted Sep. 30, 1999.

Mozayani, Ashraf, et al.; "Distribution of Topiramate in a Medical Examiner's Case," *Journal of Analytical Toxicology*, vol. 23, Oct. 1999.

Riffitts, J.M., et al.; "A capillary gas chromatographic assay with nitrogen phosphorus detection for the quantification of topiramate in human plasma, urine and whole blood," *Journal of Pharmaceutical and Biomedical Analysis*, 19 (1999) 363-371; received Nov. 8, 1996; accepted May 8, 1998.

Holland, Mary L., et al.; "Automated capillary gas chromatographic assay using flame ionization detection for the determination of topiramate in plasma," *Journal of Chromatography*, 433 (1988) 276-281; first received May 16, 1988; revised manuscript received Aug. 1, 1988.

(Continued)

*Primary Examiner*—Shafiqul Haq
(74) *Attorney, Agent, or Firm*—Workman Nydegger

(57) ABSTRACT

Generally, the present invention relates to topiramate analogs that have substituents at the sulfamate group or at the 9-position or 10-position. The topiramate analogs can include immunogenic moieties that can be used to prepare anti-topiramate antibodies, or antigenic moieties that can be used in immunodiagnostic assays for topiramate. Also, the topiramate analog can include tracer moieties for detecting the presence or amount of the analog during an immunodiagnostic assay. Additionally, the topiramate analogs can be used in immunodiagnostic assays to compete with topiramate for binding with anti-topiramate antibodies.

14 Claims, 18 Drawing Sheets

OTHER PUBLICATIONS

Maryanoff, et al., "Anticonvulsant O-Alkyl Sulfamates. 2,3:4,5-Bis-O-(1-methylethylidend)-β-D-fructopyranose Sulfamate and Related Compounds," *J. Med. Chem.* (1987), 30, 880-887.
U.S. Appl. No. 11/254,598, filed Oct. 20, 2005, Ouyang et al.
U.S. Appl. No. 11,858,426, filed Sep. 20, 2007, Ouyang et al.
International Preliminary Report on Patentability, from PCT/US2005/037698, May 1, 2007, 5 pages.
Written Opinion, from PCT/US2005/037698, Feb. 17, 2006, 4 pages.
International Search Report, from PCT/US2005/037698, Mar. 14, 2006, 2 pages.
International Preliminary Report on Patentability, from PCT/US2005/038257, May 1, 2007, 6 pages.
Written Opinion, from PCT/US2005/038257, May 23, 2006, 5 pages.
International Search Report, from PCT/US2005/038257, Aug. 4, 2006, 2 pages.
Office Action dated Apr. 4, 2008, from U.S. Appl. No. 11/254,598, 10 pages.

\* cited by examiner

IMMUNOASSAYS FOR TOPIRAMATE

CROSS-REFERENCE TO RELATED APPLICATIONS

This United States Patent Application claims benefit of the U.S. Provisional Application having Ser. No. 60/621,770, entitled, "IMMUNOASSAYS FOR TOPIRAMATE, which was filed on Oct. 25, 2004, with Anlong Ouyang, Ph.D. et al. as inventors, wherein the provisional application is incorporated herein by reference.

BACKGROUND OF THE INVENTION

1. The Field of the Invention

The present invention relates to topiramate immunodiagnostic reagents and protocols. More particularly, the present invention relates to topiramate, topiramate analogs, immunogens and antigens prepared from topiramate analogs, antibodies prepared from topiramate-based immunogens, and methods of making and using the same.

2. The Related Technology

Topiramate is chemically represented as 2,3:4,5-bis-O-(1-methyl-ethyliden-β-D-fructopyranose sulfamate or 2,3:4,5-di-O-isopropylidene-beta-D-fructopyranose sulfamate, which is shown below. Topiramate is an anti-epileptic drug ("AED"), and is chemically unrelated to many existing AEDs. Topiramate, which is the active ingredient in TOPAMAX®, was approved by the FDA in 1996 for use as adjunctive therapy in the treatment of adults with partial seizures with or without secondary generalization, and may also be useful for Lennox-Gastaut syndrome and infantile spasms.

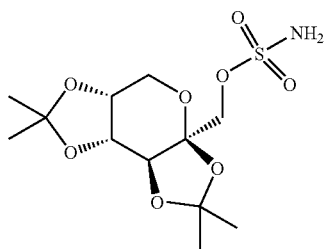

Topiramate

It is well known that various drugs, such as AEDs, can have different pharmacokinetic and/or pharmacodynamic profiles in different patient populations, which results in the therapeutic drug monitoring ("TDM") of AEDs to be vitally important. One goal of a TDM program is to optimize a patient's clinical outcome by managing and/or optimizing a medication regimen with the assistance of determining drug concentrations at various times after administration. Accordingly, the drug dose and regimen can be modulated for a single patient or patient population based on TDM.

Several characteristics of topiramate suggest there is a clinical need to individualize patient therapy by use of TDM. It has been suggested that there are large inter-individual variations in dose versus serum concentrations in patients. Also, pharmacokinetic variability plays a major role in the topiramate dosage requirements that are needed to achieve optimum serum concentrations.

It as been suggested that an appropriate range of optimal serum concentrations for topiramate would be 7 to 24 µmol/L in patients receiving a topiramate dose of 125 to 400 mg in addition to other AEDs. Some patients receiving considerably higher doses, which can be up to 2000 mg, had systemic topiramate concentrations as high as 80 µmol/L. Effective TDM can be used to predict dosing regimens that can obtain appropriate topiramate concentrations within the therapeutic index.

Additionally, dose escalation add-on studies have been performed with topiramate with the intention of proceeding to monotherapy where possible. Accordingly, morning trough serum topiramate concentrations were taken and related to seizure control and associated side effects. Results indicated a clear improvement in seizure control with serum topiramate concentration in the range of 15 to 75 µmol/L, but a reduction in seizure control was seen at serum concentrations greater than 75 µmol/L. Also, there was a significant increase in side effects with serum concentrations greater then 60 µmol/L. Thus, a tentative target serum concentration range for topiramate of about 15 to 60 µmol/L has been suggested; however, most patients can have serum concentrations in the low to mid range with an appropriate dose regimen.

Many methods have been described for determining the systemic concentration of topiramate in a patient. See, Berry D J, et al. *Ther Drug Monit;* 22:460-4 (2000). Capillary gas chromatographic methods have described the determination of topiramate in serum using flame-ionizing detection and nitrogen-specific detection. See, Holland et al., *J Chromatogr;* 433:276-281 (1988), and Riffits et al., *J Pharm Biomed Anal;* 19:363-371 (1999), Tang et al., *Ther Drug Monitoring;* 22:195-201 (2000). Additionally, methods for using GLC or HPLC with MS have been shown to measure topiramate concentrations. See, Mozayani A, et al. *J Anal Toxicol;* 23:556-558 (1999), Chen S, et al., *J Chromatogr;* 761: 133-7 (2001), and Christensen et al., *Ther Drug Monitoring;* 24:658-664 (2002). However, such methods are impractical for commercial use due to, for example, long sample preparation time, long assay time, high cost, and labor-intensive procedures. Thus, a simple and fast analytical method for measuring topiramate plasma levels is needed for effective TDM.

Topiramate can be measured in plasma or serum using a commercially available (Seradyn, Inc.) FPIA immunoassay. See, U.S. Pat. No. 5,952,187, which is included herein by reference. While the current FPIA immunoassay is simple and fast, the immunoassay is limited by poor availability of previous topiramate analogs and poor user functionality.

Immunoassay techniques have been developed to detect various drugs in biological samples and are well suited for such commercial analytical applications. Accordingly, immunoassays can be used to quickly determine the amount of a drug and/or drug metabolite in a patient's blood. Examples of immunoassays can include, but not limited to, homogeneous microparticle immunoassay (e.g., immunoturbidimetric) or quantitative microsphere systems ("QMS®"), fluorescence polarization immunoassay ("FPIA"), cloned enzyme donor immunoassay ("CEDIA"), chemiluminescent microparticle immunoassay ("CMIA"), and the like.

Accordingly, it would be advantageous to have immunoassays configured to detect topiramate in a patient's blood, serum, plasma, and/or other biological fluids or samples. Additionally, it would be advantageous to have topiramate analogs for use in such immunoassays, and/or topiramate analog-based immunogens for use in producing anti-topiramate antibodies.

BRIEF SUMMARY OF THE INVENTION

Generally, the present invention relates to topiramate analogs and immunodiagnostic assays for topiramate. The topiramate analogs can include operative groups, such as immunogenic moieties that can be used to prepare anti-topiramate antibodies; antigenic moieties that can be used in immunodiagnostic assays for topiramate; or tracer moieties that can be used in immunodiagnostic assays. Additionally, the topiramate analogs can be used in immunodiagnostic assays to compete with topiramate for anti-topiramate antibodies.

In one embodiment, the present invention includes a topiramate analog having a chemical structure of one of Formula 1 or Formula 2, below.

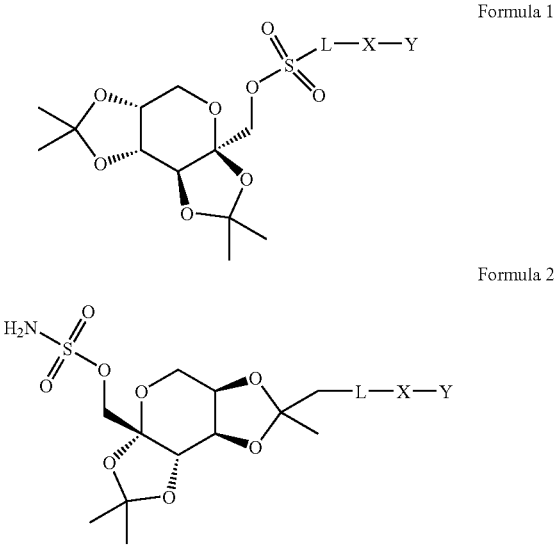

Formula 1

Formula 2

The topiramate analogs shown in Formula 1 and Formula 2 can be characterized by L being one of the groups $SO_2NH$ $(CH_2)_2NH$, NHCO, $NHCH_2Ph$, COO, or O. Additionally, X can be at least one of a bond between L and Y, substituted or unsubstituted aromatic or aliphatic groups having from 1 to 2 rings, or a saturated or unsaturated, substituted or unsubstituted, and straight or branched chain having from 1 to 20 carbon or hetero chain atoms, and most preferably 1-10 carbon or hetero atoms. Also, Y can be selected from the group consisting of aliphatic, alcohol, amine, amide, carboxylic acid, aldehyde, ester, activated ester, aliphatic ester, imidoester, isocyanate, isothiocyanate, anhydride, thiol, thiolactone, diazonium and maleimido groups.

Additionally, Y can be a linker group coupled to an operative selected from the group consisting of proteins, lipoproteins, glycoproteins, polypeptides, polysaccharides, nucleic acids, polynucleotides, teichoic acids, radioactive isotopes, enzymes, enzyme fragments, enzyme donor fragments, enzyme acceptor fragments, enzyme substrates, enzyme inhibitors, coenzymes, catalysts, fluorescent moieties, phosphorescent moieties, anti-stokes up-regulating moieties, chemiluminescent moieties, luminescent moieties, dyes, sensitizers, particles, microparticles, magnetic particles, solid supports, liposomes, ligands, receptors, hapten radioactive isotopes, and combinations thereof. More preferably, the operative group is selected from the group consisting of albumins, serum proteins, globulins, ocular lens proteins, bovine serum albumin, keyhole limpet hemocyanin, egg ovalbumin, bovine gamma-globulin, synthetic polypeptides, starches, glycogen, cellulose, carbohydrate gums, gum arabic, agar, polynucleotide, particles having a diameter of at least about 0.02 microns to about 100 microns, cells, erythrocytes, leukocytes, lymphocytes, *Streptococcus, Staphylococcus aureus, E. coli*, viruses, liposomes, latex, phospholipids vesicles, cationic liposomes, anionic liposomes, lipoproteins, and lipopolymers. Most preferably, the operative group is at least one of albumin, human serum albumin, bovine serum albumin, keyhole limpet hemocyanin, or chemiluminescent moiety such as a fluorescent moiety.

In one embodiment, the analog can be coupled to an immunogenic moiety to form an immunogen that generates an antibody at a titer sufficient for use in an immunodiagnostic assay for topiramate. Also, the analog can be coupled to an immunogenic moiety to form an immunogen that generates an antibody that interacts with the analog and topiramate. The analog can also be coupled to a tracer moiety and have sufficient solubility for use in an immunodiagnostic assay. Additionally, the analog can be coupled to an antigen moiety and have sufficient solubility for use in an immunodiagnostic assay. Further, the analog can be stably loaded onto or coupled with a particle or microparticle or coupled to an enzyme, enzyme donor, or enzyme acceptor. Furthermore, the analog is capable of competing with topiramate for interacting with an anti-topiramate antibody.

In one embodiment, a method of making a topiramate analog can include reacting a topiramate halide, such as a chloride, such as a having a halide or chloride leaving group, with a reactant having a primary amine that displaces the halide or chloride leaving group to form a covalent bond with the sulfamate group. Alternatively, the analog can be made by reacting topiramate with a reactant having a carboxyl group that reacts with a primary amine to form an amide. In another alternative, the analog can be made by reacting a 9-hydroxy or 10-hydroxy topiramate with a reactant having an isocyanate functional group.

One embodiment of the present invention includes an antibody composition for use in an immunodiagnostic system for detecting the presence of topiramate in a sample. The antibody composition can include an anti-topiramate antibody having at least one binding domain, wherein the antibody is capable of binding topiramate and binding a topiramate analog. Also, the antibody can be present in a titer of at least about 1:5,000, more preferably at least about 1:10,000, even more preferably at least about 1:50,000, still more preferably at least about 1:100,000, and most preferably at least about 1:300,000. In some instances it can be preferable to have an antibody titer as low as 1:5,000 or as high as 1:300,000.

Additionally, the antibody can be a monoclonal antibody and/or a polyclonal antibody. The antibody can have at least one of affinity, specificity, or avidity for a topiramate analog compared to topiramate that is sufficient for use in a homogeneous, heterogeneous, or other immunodiagnostic assay. As such, the interaction between the antibody and the topiramate analog can be at least 50% of at least one of affinity, specificity, or avidity of the antibody for topiramate, even more preferably at least 70% of at least one of affinity, specificity, or avidity of the antibody for topiramate, most preferably at least 90% of at least one of affinity, specificity, or avidity of the antibody for topiramate. Optionally, at least one of affinity, specificity, or avidity of the antibody for a topiramate analog is substantially the same as for topiramate.

In one embodiment, the present invention includes a system for use in an immunodiagnostic assay for detecting the presence of topiramate in a sample. Such a system can include the topiramate analog and the anti-topiramate antibody. Additionally, one of the topiramate analog or anti-topiramate antibody can be coupled with one of a particle, magnetic particle, microparticle, microsphere, support, enzyme donor, or enzyme acceptor.

In one embodiment, the system can include at least one of the following: (a) a stock composition of topiramate; (b) a series of compositions containing topiramate at different concentrations, the series of compositions forming a concentration gradient; (c) the topiramate analog coupled to a tracer moiety; (d) the topiramate analog coupled to a microparticle; (e) the antibody coupled to a microparticle; (f) the topiramate analog coupled to an enzyme donor along with a corresponding enzyme acceptor; (g) the topiramate analog conjugated to an enzyme acceptor along with a corresponding enzyme donor; or (h) the antibody coupled to a particle suitable for separation by filtration or sedimentation.

The present invention also includes methods of performing immunodiagnostic assays for detecting the presence of topiramate in a sample. Such methods can include combining an anti-topiramate antibody and a topiramate analog with a sample obtained from a subject previously administered topiramate to form a first composition. Any free topiramate from the sample and the topiramate analog are then allowed to compete for binding with the antibody. After the competitive binding, the binding between the topiramate analog and the antibody is detected.

In one embodiment, the immunodiagnostic assay uses a topiramate analog including a fluorescent moiety and is combined with the antibody and sample as described. The fluorescent moiety can be excited with polarized light having a first amount of polarization, and the polarized light emitted from the fluorescent moiety having a second amount of polarization is detected. Optionally, the first amount of polarization is compared with the second amount of polarization, and a determination is made as to whether topiramate is present in the sample, wherein the second amount of polarization being different from the first amount of polarization is an indication that topiramate is present in the sample. Additionally, the immunodiagnostic assay can include a control by combining a known amount of topiramate with the topiramate analog and antibody to form a control binding composition. The polarized light emitted from the fluorescent moiety in the control binding composition having a third amount of polarization is detected, and compared with the second amount of polarization. The amount of topiramate present in the sample is then determined.

In one embodiment, an immunodiagnostic assay uses a topiramate analog or antibody coupled to a microparticle. The analog, antibody, and sample are combined into a first composition, where any free topiramate competes with the analog for binding with the antibody. The first composition is then irradiated with incident light, and a first intensity of light transmitted from the first composition is detected. The minimum intensity of light transmitted from a control binding composition having the topiramate analog and antibody and not having free topiramate is identified and compared with the first intensity of the transmitted light. A determination is made as to whether topiramate is present in the sample, wherein the minimum intensity being different from the first intensity is an indication that topiramate is present in the sample. Additionally, the immunodiagnostic assay can include another control by combining a known amount of topiramate with the topiramate analog and antibody to form a second control binding composition. The second control binding composition is then irradiated with incident light, and a second intensity of light transmitted from the second control binding composition is detected. The amount of topiramate present in the sample can then be determined, wherein a comparison between the first intensity and the second intensity is an indication of the amount of topiramate present in the sample.

In one embodiment, an immunodiagnostic assay uses a topiramate analog having an enzyme donor. The analog, antibody, and sample are combined into a first composition, where any free topiramate competes with the analog for binding with the antibody. An enzyme acceptor and substrate are combined with the first composition, wherein the substrate is cleavable by interacting with the enzyme donor and enzyme acceptor. The enzyme activity is then detected. Additionally, the immunodiagnostic assay can include a control by combining a known amount of topiramate with the topiramate analog and antibody to form a control binding composition, and the enzyme acceptor and substrate are then combined therewith. The amount of topiramate present in the sample is determined by a comparison between the enzyme activity and the control enzyme activity providing an indication of the amount of topiramate present in the sample.

In one embodiment, an immunodiagnostic assay uses a topiramate analog having a tracer moiety and an antibody coupled with a particle. The analog, antibody, and sample are combined into a first composition, where any free topiramate competes with the analog for binding with the antibody. The antibody is separated from the first composition, and any unbound topiramate analog is separated from the antibody. The tracer moiety bound with the antibody from the first composition is then detected. Additionally, the immunodiagnostic assay can include a control by combining a known amount of topiramate with the topiramate analog and antibody to form a control binding composition. Accordingly, the amount of topiramate present in the sample can be determined by a comparison between the amount of tracer moiety in the first composition and the amount of tracer moiety in the control binding composition in order to provide an indication of the amount of topiramate present in the sample.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
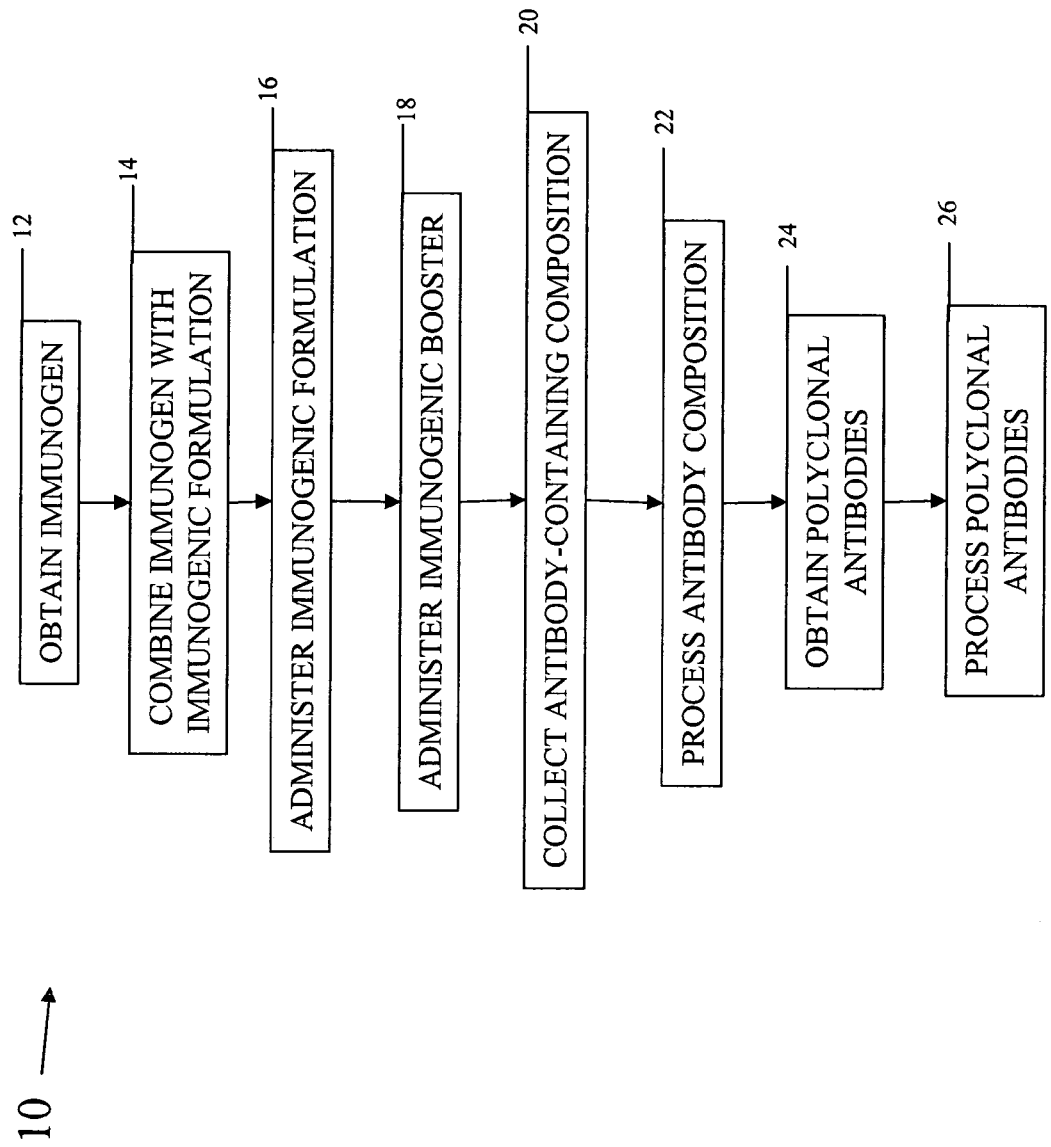
FIG. 1 is a flow diagram illustrating an embodiment of a method for preparing an anti-topiramate antibody.

Generally, the present invention relates to topiramate analogs and immunodiagnostic assays for topiramate. The topiramate analogs can include immunogenic moieties that can be used to prepare anti-topiramate antibodies, or antigenic moieties, or tracer moieties that can be used in immunodiagnostic assays for topiramate. Additionally, the topiramate analogs can be used in immunodiagnostic assays to compete with topiramate for anti-topiramate antibodies. As such, the following terminology is meant to describe embodiments of the invention, and is not intended to be limiting.

As used herein, the term "hapten" is meant to refer to a partial or incomplete antigen, and can be a small molecule or drug. Also, a hapten can be a low molecular weight molecule that is a protein-free or polypeptide-free substance. Usually, a hapten is not capable of stimulating antibody formation alone, but can be capable of interacting with antibodies. Accordingly, topiramate and topiramate analogs in accordance with the present invention can be haptens.

As used herein, the term "analog" or "derivative" is meant to refer to a chemical compound or molecule made from a parent compound or molecule by one or more chemical reactions. As such, an analog can be a compound with a structure similar to that of topiramate or based on a topiramate scaffold, but differing from it in respect to certain components or structural makeup, which may have a similar or opposite action metabolically. An analog or derivative of topiramate in accordance with the present invention can be used to compete for binding with an antibody that recognize both the analog and topiramate. Also, an analog can include an operative group coupled to topiramate through a linker group.

As used herein, the terms "immunogen" and "immunogenic" are meant to refer to substances capable of producing or generating an immune response in an organism. An immunogen can also be antigen. Usually, an immunogen has a fairly high molecular weight (e.g., greater than 10,000), thus, a variety of macromolecules such as proteins, lipoproteins, polysaccharides, some nucleic acids, and certain of the teichoic acids, can be coupled to a hapten in order to form an immunogen in accordance with the present invention.

As used herein, the term "immunogenicity" is meant to refer to the ability of a molecule to induce an immune response, which is determined both by the intrinsic chemical structure of the injected molecule and by whether or not the host animal can recognize the compound. Small changes in the structure of an antigen can greatly alter the immunogenicity of a compound and have been used extensively as a general procedure to increase the chances of raising an antibody, particularly against well-conserved antigens. For example, these modification techniques either alter regions of the immunogen to provide better sites for T-Cell binding or expose new epitopes for B-cell binding.

As used herein, the terms "carrier," "immunogenic moiety," or "immunogenic carrier," are meant to refer to an immunogenic substance, commonly a protein, which can be coupled to a hapten. An immunogenic moiety coupled to a hapten can induce an immune response and elicit the production of antibodies that can bind specifically with the hapten. Immunogenic moieties are operative groups that include proteins, polypeptides, glycoproteins, complex polysaccharides, particles, nucleic acids, polynucleotides, and the like that are recognized as foreign and thereby elicit an immunologic response from the host. Additionally, linkers can comprise modified or unmodified nucleotides, nucleosides, polymers, sugars and other carbohydrates, polyethers such as, for example, polyethylene glycols, polyalcohols, polypropylenes, propylene glycols, mixtures of ethylene and propylene glycols, polyalkylamines, polyamines such as spermidine, polyesters such as poly(ethyl acrylate), polyphosphodiesters, and alkylenes. An example of an operative group and its linker is cholesterol-TEG-phosphoramidite, wherein the cholesterol is the operative group and the tetraethylene glycol and phosphate serve as linkers.

In one example, an immunogenic carrier can be coupled with a hapten in order to stimulate immunogenicity and antibody formation against the hapten. Usually, immunogenic carriers are large molecules that are highly immunogenic and capable of imparting immunogenicity to a hapten. For example, a protein can be used as an immunogenic carrier because foreign proteins can elicit such an immunological response. Protein carriers can be highly soluble and include functional groups that could facilitate easy conjugation with a hapten molecule. Some of the most common carrier proteins in use today are keyhole limpet hemocyanin (KLH, MW 450,000 to 13,000,000), and bovine serum albumin (BSA, MW 67,000). Keyhole limpet hemocyanin is the oxygen-carrying protein of the marine keyhole limpet, and is extremely large and exhibits increased immunogenicity when it is disassociated into subunits, probably due to exposure of additional epitopic sites to the immune system. BSA is highly soluble protein containing numerous functional groups suitable for conjugation.

As used herein, the term "antibody" is meant to refer to a protein that is produced in response to the presence of foreign molecules in the body. They can be characterized by their ability to bind both to antigens and to specialized cells or proteins of the immune system. Antibodies are divided into five classes, IgG, IgM, IgA, IgE, and IgD, and are immunoglobulin produced by plasma cells.

As used herein, the term "epitope" is meant to define the region of an antigen that interacts with an antibody. Accordingly, a molecule or other substance, which is an antigen, can include at least one epitope with antibody activity. This can allow for an antigen to have various epitopes recognized by the same or different antibody. Also, an epitope is not an intrinsic property of any particular structure, but can be defined as a binding site that interacts with the antibody.

As used herein, the term "affinity" is meant to refer to a measure of the strength of binding between an epitope and an antibody. Accordingly, a single antibody can have a different affinity for various epitopes. This can allow a single antibody to bind strongly to one epitope and less strongly to another. As such, an antibody can have a first affinity to a drug, such as topiramate, and have a second affinity to a topiramate analog. However, it is possible for the antibody to have substantially equivalent or similar affinity for both topiramate and a topiramate analog, which allows the analog to be used to generate antibodies for topiramate, and their use in competitive binding studies. Thus, topiramate analogs in accordance with the present invention can be used to generate antibodies with affinity for topiramate.

As used herein, the term "avidity" is meant to refer to a measure of the overall stability of the complex between antibodies and antigens. The overall stability of an antibody-antigen interaction can be governed by three major factors as follows: (a) the intrinsic affinity of the antibody for the epitope; (b) the valency of the antibody and antigen; and (c) the geometric arrangement of the interacting components. As such, the avidity of the antibody-antigen complex can be modulated by varying the foregoing parameters, as well as others.

As used herein, the term "specificity" is meant to refer to the preferential binding of an antibody with an epitope in comparison with other available epitopes. That is, the specificity of an antibody can preferentially bind topiramate and/or analog instead of a topiramate metabolite. This can be used to generate anti-topiramate antibodies that preferentially bind with topiramate over its metabolites so that the true concentration of topiramate can be assessed so as to not be contaminated by adverse antibody-metabolite binding. Also, the specificity of an antibody for binding with topiramate can be used to tailor analogs with similar or substantially the same specificity as topiramate.

As used herein, the terms "on rate," "off rate," or "on-off rate" are meant to refer to ways of describing the kinetics of an antibody-antigen interaction. That is, the "on rate" is meant to refer to the Ka (i.e., association constant) and the "off rate" is meant to refer to the Kd (i.e., dissociation constant). Each antibody has a Ka for a particular antigen or epitope, which is usually referred to as affinity or strength of binding. With regard to a polyclonal antibody, the "ON-Off rate" is meant to refer to a sum of many different Kas and or Kds, for each particular antibody that form the polyclonal antibody.

As used herein, the term "polyclonal antibody" is meant to refer to a heterogeneous mixture of antibodies with a wide range of specificities and affinities to a given antigen or epitope. Thus, the polyclonal antibody, which can also be referred to as polyclonal antibodies, can include a plurality of antibodies, each distinguishable from the others, that bind or otherwise interact with an antigen. The different antibodies that comprise a polyclonal antibody can be produced or generated by injecting an immunogen having an epitope into an animal and, after an appropriate time, collecting and optionally purifying the blood fraction containing the antibodies of interest. In producing antibodies, several parameters can be considered with respect to the final use for the polyclonal antibody. These parameters include the following: (1) the specificity of the antibody (i.e., the ability to distinguish between antigens); (2) the avidity of the antibody (i.e., the strength of binding an epitope); and (3) the titer of the antibody, which determines the optimal dilution of the antibody in the assay system.

As used herein, the term "monoclonal antibody" is meant to refer to an antibody that is isolated from a culture of normal antibody-producing cells and one progenitor cell. A monoclonal antibody can have a homogeneous binding constant, and are well known in the art.

As used herein, the term "Bmax" is meant to refer to the maximum binding between an antibody and a ligand (e.g., analog, antigen, label, etc.) independent of the titer. Also, Bmax can be related to avidity, but can also be independent of avidity, and can be used in an assessment for determining of how well an antibody can bind a ligand and give measurable signals. Additionally, Bmax can be determined as the maximal absorbance of each specimen and is used to calculate Bo. The value of Bmax can vary as high as 3-4 OD, and can be higher for a monoclonal antibody program.

As used herein, the term "Bo" is meant to refer to an absorbance selection for a binding displacement assay, and is about 30% to 50% of the Bmax for the displacement assay. As such, Bo can be used to quickly measure off-rate, which can be used to assay for avidity. Also, 50% Bmax can be the used when the OD is about half of Bmax, which can generally range from 1.7 to 1 OD. At times, 50% Bmax can have an OD that is as high as 1.7, which can be too saturated with antibody for accurate measurements and often leads to poor displacement. Thus, 30% Bmax can be used in the instance the antibody is still too saturated. In order to produce suitable Bo values and displacement data, Bmax can be within 2.0 and 2.5 OD, and Bo can be within 1.0 an 1.25 OD.

As used herein, the terms "immunoassay" or "immunodiagnostic" are meant to refer to laboratory techniques that make use of the binding between an antigen and an antibody in order to identify and/or quantify at least one of the specific antigen or specific antibody in a biological sample. Currently, there are three classes of immunoassay, which are described as follows: (1) antibody capture assays; (2) antigen capture assays; and (3) two-antibody sandwich assays. Additionally, it is contemplated that new immunoassays will be developed and will be capable of employing the analogs and antibodies of the present invention.

As used here, the term "competitive immunoassay" is meant to refer to a experimental protocol in which a known amount of an identifiable antigen competes with another antigen for binding with an antibody. That is, a known antigen that binds with a known antibody is combined with a sample that is suspected of containing another antigen that also binds with the known antibody. This allows for the known antigen and another antigen to both compete for the binding site on the antibody. For example, a topiramate analog that binds with an anti-topiramate antibody can be combined with a sample suspected of containing topiramate, and the analog and topiramate compete for binding with the anti-topiramate antibody. The competition for binding with the antibody can then be used to determine whether or not topiramate is present in the sample, and can further be used to quantify the amount of topiramate in the sample.

As used herein, the term "turbidimetric detection" is meant to refer to the measurement of a decrease in the intensity in the transmission, or an increase in absorbance, of incident light due to light scattered by agglutinated particles. A decrease in intensity of transmitted light is measured against a higher starting background intensity of transmitted light. Usually, the reading is made with a detector in line with the light source, wherein the agglutination of particles inhibits transmission of the light. Therefore, the inhibition or promotion of agglutination can be used as a means for assessing the presence of a target analyte, such as topiramate. Turbidimetric assays may be easily adapted to a variety of clinical analyzers.

As used herein, the term "microparticle agglutination assays" is meant to refer to immunoassays that use the principle of inhibiting agglutination of microparticles by a target analyte. That is, decreased agglutination is attributed to the presence of the target analyte. For example, a derivative of the target drug is covalently linked to the surface of microparticle and/or the sensitized particles are agglutinated by a monoclonal antibody. When a sample contains free drug the agglutination is inhibited in proportion to the drug concentration, which leads to a classic inhibition curve relating drug concentration to absorbance.

As used herein, the term "therapeutic concentration" is meant to refer to the concentration of a drug that is effective in producing a desired clinical effect.

As used herein the term "operative group" is meant to refer to a molecule or macromolecule coupled to topiramate through a linker group. An operating group can include immunogenic moiety, antigen moiety, tracer moiety, and the like.

As used herein, the terms "active ester" or "activated ester" are meant to refer to an ester group that can react with a free amino group of a compound such as, for example, peptides and proteins. An active ester can include a carboxyl group linked to an active leaving group. Often, the active leaving group includes the ester oxygen so the active leaving group removes the ester oxygen. For example, an active ester is susceptible to being displaced by a primary amine, which results in the removal of the ester oxygen and formation of an amide group. Examples of active leaving groups that form active esters include N-hydroxysuccinimide (referred to herein as "NHS"), p-nitrophenyl, pentafluorophenyl, N-hydroxybenzotriazolyl, and the like.

As used herein, the terms "label," "detector molecule," or "tracer" are meant to refer to any molecule which produces, or can be induced to produce, a detectable signal. The label can be conjugated to topiramate, topiramate analog, hapten, analyte, immunogen, antibody, or to another molecule such as a receptor or a molecule that can bind to a receptor. Non-limiting examples of tracers include radioactive isotopes, enzymes, enzyme fragments, enzyme substrates, enzyme inhibitors, coenzymes, catalysts, fluorophores, dyes, chemiluminescers, luminescers, sensitizers, non-magnetic or magnetic particles, solid supports, liposomes, ligands, receptors, hapten radioactive isotopes, and the like. As described herein, the analogs can also be coupled to a variety of labels by methods well known in the art to provide a variety of reagents useful in various immunoassay formats. For detecting the results of the immunoassays, detector molecules such as fluorophores, for example, fluorescein, radio-labels, or chemiluminescent groups can be coupled to the analogs to produce tracers.

As used herein, the terms "linking group" or "linker" are meant to refer to a portion of a chemical structure that connects two or more substructures such as topiramate or a topiramate analog, with an operative group. A linking group can have at least one uninterrupted chain of atoms other than hydrogen (or other monovalent atoms) extending between the substructures. Usually, a linking group includes a chain of carbon atoms or hetero atoms, which can be substituted or unsubstituted. The atoms of a linking group and the atoms of a chain within a linking group can be interconnected by chemical bonds. For example, linkers maybe straight or branched, substituted or unsubstituted, saturated or unsaturated chains, wherein the chain atoms can include carbon and/or hetero atoms. This can include one or more hetero atoms within the chain or at termini of the chains. Additionally, a linking group may also include cyclic and/or aromatic groups as part of the chain or as a substitution on one of the atoms in the chain. The number of atoms in a linking group or linker is determined by counting the atoms other than hydrogen in the backbone of the chain, which is the shortest route between the substructures being connected. Linking groups may be used to provide an available site on a hapten for conjugating a hapten with an operative group such as a tracer, label, carrier, immunogenic moiety, and the like.

As used herein, the term "hetero atoms" is meant to refer to atoms other than carbon atoms such as oxygen, nitrogen, sulfur, phosphorus, and the like. Usually, a heteroatom is multivalent so as to form at least two covalent bonds, which can be used in a linking group or other moiety.

The topiramate analogs can include a topiramate molecule conjugated to a moiety. The moiety can be any of a wide range of chemical compounds that can modify the physicochemical properties of topiramate. Also, the moiety can be used as a linker or conjugate a linking group to the topiramate. Accordingly, the moiety can be comprised of an alkyl, aliphatic, straight chain aliphatic, branched aliphatic, substituted aliphatic, cyclic aliphatic, heterocyclic aliphatic, aromatic, heteroaromatic, polyaromatic, and the like.

As used herein, the term "aliphatic" is meant to refer to a hydrocarbyl moiety, such as an alkyl group, that can be straight or branched, saturated or unsaturated, and/or substituted or unsubstituted, which has twenty or less carbons in the backbone. An aliphatic group may comprise moieties that are linear, branched, cyclic and/or heterocyclic, and contain functional groups such as ethers, ketones, aldehydes, carboxylates, and the like. Exemplary aliphatic groups include but are not limited to substituted and/or unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, alkyl groups of higher number of carbons and the like, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, and the like. The terms aliphatic or alkyl also encompasses alkenyl groups, such as vinyl, allyl, aralkyl and alkynyl groups.

Substitutions within an aliphatic group can include any atom or group that can be tolerated in the aliphatic moiety, including but not limited to halogens, sulfurs, thiols, thioethers, thioesters, amines (primary, secondary, or tertiary), amides, ethers, esters, alcohols, oxygen, and the like. The aliphatic groups can by way of example also comprise modifications such as azo groups, keto groups, aldehyde groups, carbonyl groups, carboxyl groups, nitro, nitroso or nitrile groups, heterocycles such as imidazole, hydrazino or hydroxylamino groups, isocyanate or cyanate groups, and sulfur containing groups such as sulfoxide, sulfone, sulfide, and disulfide. Additionally, the substitutions can be via single, double, or triple bonds, when relevant or possible.

Further, aliphatic groups may also contain hetero substitutions, which are substitutions of carbon atoms, by hetero atoms such as, for example, nitrogen, oxygen, phosphorous, or sulfur. As such, a linker comprised of a substituted aliphatic can have a backbone comprised of carbon, nitrogen, oxygen, sulfur, phosphorous, and/or the like. Heterocyclic substitutions refer to alkyl rings having one or more hetero atoms. Examples of heterocyclic moieties include but are not limited to morpholino, imidazole, and pyrrolidino.

As used herein, the term "aromatic" is meant to refer to molecule is one in which electrons are free to cycle around circular or cyclic arrangements of atoms, which are alternately singly and doubly bonded to one another. More properly, these bonds may be seen as a hybrid of a single bond and a double bond, each bond in the ring being identical to every other. Examples of aromatic compounds that can be present in topiramate analogs include benzene, benzyl, toluene, xylene, and the like. The aromatic compound can include hetero atoms so as to be a hetero aromatic such as pyridine, furan, tetrahydrofuran, and the like. Also, an aromatic can be a polycyclic aromatic such as naphthalene, anthracene, phenanthrene, polycyclic aromatic hydrocarbons, indole, quinoline, isoquinoline, and the like.

As used herein, the term "amine" is meant to refer to moieties that can be derived directly or indirectly from ammonia by replacing one, two, or three hydrogen atoms by other groups, such as, for example, alkyl groups. Primary amines have the general structures $RNH_2$ and secondary amines have the general structure $R_2NH$. The term amine includes, but is not limited to methylamine, ethylamine, propylamine, isopropylamine, aniline, cyclohexylamine, benzylamine, polycyclic amines, heteroatom substituted aryl and alkylamines, dimethylamine, diethylamine, diisopropylamine, dibutylamine, methylpropylamine, methylhexylamine, methylcyclopropylamine, ethylcylohexylamine, methylbenzylamine, methycyclohexylmethylamine, butylcyclohexylamine, morpholine, thiomorpholine, pyrrolidine, piperidine, 2,6-dimethylpiperidine, piperazine, and heteroatom substituted alkyl or aryl secondary amines.

As used herein, the term "poly(amino acid)" or "polypeptide" is a polyamide formed from amino acids. Poly(amino acid)s will generally range from about 200-2,000 molecular weight or greater than about 2,000 molecular weight, or having no upper molecular weight limit, and normally being less than 10,000,000 and usually not more than about 600,000 daltons. There will usually be different ranges, depending on whether an immunogenic carrier or an enzyme is involved.

As used herein, the term "peptide" is meant to refer to any compound formed by the linkage of two or more amino acids by amide (peptide) bonds, usually a polymer of α-amino acids in which α-amino group of each amino acid residue (except the $NH_2$ terminus) is linked to the α-carboxyl group of the next residue in a linear chain. The terms "peptide," "polypeptide," and "poly(amino acid)" are used synonymously herein to refer to this class of compounds without restriction as to size. The largest members of this class are referred to as proteins.

As used herein, the term "biological sample" is meant to refer to a solid or fluid sample that is obtained from a biological entity. As such, a biological sample can include, but is not limited to, any quantity of a substance from a living thing or formerly living thing, such as humans and other animals. Such a substance can include, but is not limited to, blood, serum, plasma, urine, tears, cells, organs, tissues, bone, bone marrow, lymph, lymph nodes, synovial tissue, chondrocytes, synovial macrophages, endothelial cells, skin, and the like.

As used herein, the term "patient" is meant to refer to human and other animal subjects. More particularly, a patient is a human or other animal subject needing an anti-epileptic drug such as topiramate.

Additionally, the terms used herein to describe the invention can be construed using the foregoing definitions and/or definitions well known in the art. As such, the foregoing terminology is meant to describe the invention and is not intended to be limiting.

I. Topiramate Analogs

In one embodiment, the present invention relates to analogs of topiramate. As such, topiramate can be conjugated with an analog moiety at the sulfamate moiety or the 9-carbon or 10-carbon methyl group of topiramate to form an analog. The 9-carbon or 10-carbon conjugations are substantially similar in chemistry and/or functionality so as to be substantially indistinguishable in many applications, wherein reference to the 9-carbon or 9-position is meant to also refer to the 10-carbon or 10-position.

A topiramate analog can be further coupled through the analog moiety or linker to an immunogenic moiety, antigenic moiety, and/or tracer moiety, which forms another analog such as an immunogen, antigen, and/or tracer. Additionally, conjugation through the sulfamate moiety rather than the 9-carbon methyl group may be advantageous in certain instances because the portion of the topiramate analog available for antibody induction and recognition is the region that differs in the topiramate metabolite 9-hydroxytopiramate.

In one embodiment, the present invention describes novel analogs of topiramate having sulfamate conjugations. That is, the sulfamate group can be coupled to a linking moiety via the sulfur atom. The linker moiety can be considered to be the substituent that is coupled with the topiramate scaffold in order to form the analog. The linker moiety can be any of a wide array of chemical entities, which are described in more detail below. Accordingly, the sulfamate-substituted analog of topiramate can have the generic structure of Formula 1A and/or Formula 1B:

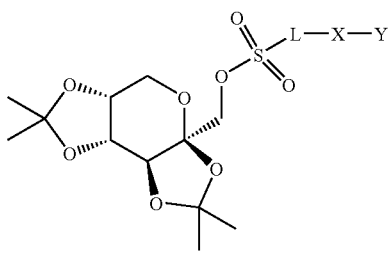

FORMULA 1A

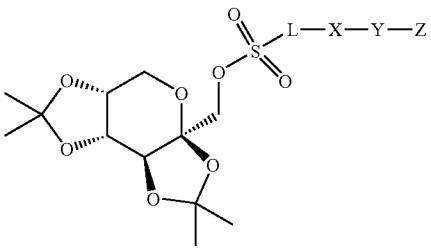

FORMULA 1B

In another embodiment, the topiramate scaffold can include a 9-substitution, which is substantially similar to a 10-substitution. Accordingly, the 9-substitution analog of topiramate can have the generic structure of Formula 2A and/or Formula 2B:

FORMULA 2A

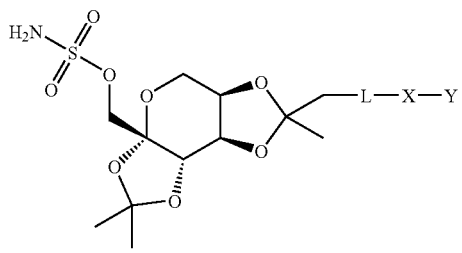

FORMULA 2B

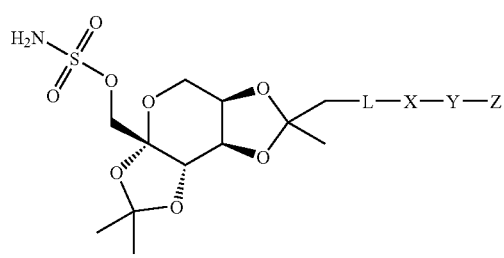

The topiramate scaffold depicted in Formulas 1A, 1B, 2A and/or 2B can be substituted with a wide range of chemical entities. Accordingly, the L group can be an O, CO, COO, $SO_2$, $CH_2$, NH, $NH(CH_2)_2NH$, NHCO, or $NHCH_2Ph$. As such, the L group can be used as a linking group to conjugate the analog moiety and/or conjugate moiety to the topiramate scaffold.

Additionally, as used in connection to Formulas 1A, 1B, 2A and/or 2D, the X group can be a saturated or unsaturated, substituted or unsubstituted, and/or straight or branched chain having 1-20 carbon or hetero atoms, or more preferably 1-10 carbon or hetero atoms. Some examples of substitution groups include primary and secondary amines, aliphatics, carbonyl groups, halogens, and the like. Also, the X group can include a cyclic group that is substituted or unsubstituted, or a substituted or unsubstituted aromatic or aliphatic group having 1-2 rings, polycyclic aromatic rings, hetero aromatic rings, and the like. The X group can also be a substituted or unsubstituted aliphatic linking group containing 1-20 or 1-10 chain atoms of carbon or hetero atoms in place of or in addition to a ring group. Furthermore, the X group can be any type of bond between L and Y. Also, X can be any combination of the foregoing groups.

The Y group can be an end group or coupling group, which can be used for coupling the linker group with an operative group, such as a carrier, label, immunogenic moiety, and the like. In some instances, the end group can be derivatized or coupled with a carrier, tracer moiety, or immunogenic moiety via chemical syntheses well known in the art, wherein the Y group can be a reactive group that is used to couple with the Z group. As such, Y can be various groups, such as aliphatics, alcohols, amines, amides, carboxylic acids, aldehydes, esters, activated esters, aliphatic esters, imidoesters, isocyanates, isothiocyanates, anhydrides, thiols, alcohols, thiolactones, diazonium groups, maleimido groups, and the like as well as groups derived therefrom. Also, Y can be a $Y_1$-Z group, wherein $Y_1$ is derived from the Y end group being coupled to the Z group.

Furthermore, the Z group can be nothing or any moiety that can be coupled to the linker moiety. As such, the L-X—Y group can be considered to be the analog moiety and the Z group can be an operating group. The linker moiety can functionally serve as a linker or linking group between the topiramate scaffold and an operative group. For example, the operative group can be a carrier, label, tracer, protein, enzyme, fluorescent compound, phosphorescent compound, thermochromic compound, photochromic compound, anti-stokes up-regulating compound, chemiluminescent material, electrochemical mediator, particle, reporter group, enzyme inhibitor, nucleic acid, polypeptide, and the like.

For example, in each of Formulas 1A, 1B, 2A and/or 2B the X group can be a bond or a chain of one or more atoms, wherein at least one atom is carbon if present. As such, X can be a covalent bond between L and Y. Illustratively, X can be any of the following groups: $CH_2$; $(CH_2)_2$; $(CH_2)_3$; $(CH_2)_4$; $(CH_2)_5$; $(CH_2)_6$; $CH_2CO$; $(CH_2)_2CO$; $(CH_2)_3CO$; $(CH_2)_4CO$; $(CH_2)_5CO$; $(CH_2)_6CO$; $CH_2COO$; $(CH_2)_2COO$; $(CH_2)_3COO$; $(CH_2)_4COO$; $(CH_2)_5COO$; $(CH_2)_6COO$; CO; COO; $COCH_2$; $CO(CH_2)_2$; $CO(CH_2)_3$; $CO(CH_2)_4$; $CO(CH_2)_5$; $CO(CH_2)_6$; $COCH_2CO$; $CO(CH_2)_2CO$; $CO(CH_2)_3CO$; $CO(CH_2)_4CO$; $CO(CH_2)_5CO$; $CO(CH_2)_6CO$; $COCH_2COO$; $CO(CH_2)_2COO$; $CO(CH_2)_3COO$; $CO(CH_2)_4COO$; $CO(CH_2)_5COO$; $CO(CH_2)_6COO$; $CO(CH_2)_2CONHCH_2$; $CO(CH_2)_2CONH(CH_2)_2$; Ph; $CONHCH_2Ph$; $CONH(CH_2)_3$; $CONH(CH_2)_3CO$; $CONH(CH_2)_3COO$; $NHCH_2$; $NH(CH_2)_2$; $NH(CH_2)_3$; $NH(CH_2)_4$; $NH(CH_2)_5$; $NH(CH_2)_6$; $NHCH_2CO$; $NH(CH_2)_2CO$; $NH(CH_2)_3CO$; $NH(CH_2)_4CO$; $NH(CH_2)_5CO$; $NH(CH_2)_6CO$; $NHCH_2COO$; $NH(CH_2)_2COO$; $NH(CH_2)_3COO$; $NH(CH_2)_4COO$; $NH(CH_2)_5COO$; $NE(CH_2)_6COO$; $NHCO(CH_2)_2$; $NHCO(CH_2)_6$; $NHCO(CH_2)_2CO$; $HCO(CH_2)_6CO$; $NHCO(CH_2)_2COO$; or $NHCO(CH_2)_6COO$; combinations thereof; and the like. More preferably, X can be selected from the group consisting of $CH_2$, $(CH_2)_2$, $(CH_2)_3$, $CH_2COO$, $(CH_2)_2CO$, $(CH_2)_2COO$, $(CH_2)_3CO$, $(CH_2)_3COO$, $CO(CH_2)_6$, $CO(CH_2)_6CO$, $CO(CH_2)_6COO$, CO, COO, Ph, $CONH(CH_2)_3$, $CONH(CH_2)_3CO$, $CONH(CH_2)_3COO$, combinations thereof, and the like.

For example, in each of Formulas 1 and 2 the Y group can comprise an end group or linker derived from the end group and is always present. Illustratively, Y can be any of the following end groups or a linker group derived therefrom: COOH (carboxylic acid); COO; COO—NHS(NHS active ester); NHS; tertbutyl (t-butyl); COO-tertbutyl; OH; O—NHS(NHS active ester linker); $COOCH_2CH_3$; $COOCH_3$; $OCH_2CH_3$; $OCH_3$; NH; $NH_2$; NHCO (amide); combinations thereof; and the like. More preferably, when Y is an end group, it can be selected from the group consisting of NHS, COOH, COO—NHS, COO-tertbutyl, tertbutyl, OH, O—NHS, $COOCH_2CH_3$, $COOCH_3$, $OCH_2CH_3$, $OCH_3$, or $NH_2$. On the other hand, when Y is a linker, it is $Y_1$-Z, wherein $Y_1$ can be preferably selected from the group consiting of is at least one of COO, CO, O, CONH, or NH and Z is a macromolecule.

Accordingly, the Z group or operative group can be a carrier, tracer, or a label, such as protein, enzyme, fluorescent compound, chemiluminescent material, electrochemical mediator, particle, reporter group, enzyme inhibitor, and/or nucleic acid. Illustratively, Z can be any of the following macromolecule groups: (a) BSA; (b) KLH; (c) fluorescent tracer; and (d) the like.

Generally, the analogs can include a variety of operative groups by methods well known in the art to provide a variety of reagents useful in various immunoassay formats. As such, detector molecules, such as fluorophores, radio-labeled, or chemiluminescent groups, can be used to produce tracers. The analogs can also be bound to microparticles, such as colored latex, for use in spectrophotometric or direct optical detection formats such as in latex agglutination and chromatographic strip tests. The operative group may also be an indirect detection molecule, such as an energy transfer partner, enzyme or other group, which is detected by further chemical reactions.

Accordingly, coupling an operative group with the analog can be accomplished by any chemical reaction that will couple the operative group. This linkage or coupling can include many chemical mechanisms, for instance covalent binding, affinity binding, intercalation, coordinate binding, and complexing. Most often, the linkage or coupling is made through covalent bonding. Covalent binding can be achieved either by direct condensation of existing side chains or by incorporation of external bridging molecules. Many bivalent or polyvalent linking agents can be useful in coupling protein molecules, such as a carrier, to the analog. Representative coupling agents include organic compounds such as thioesters, carbodiimides, N-hydroxysuccinimide esters, diisocyanates, glutaraldehyde, diazobenzenes, and hexamethylene diamines; however, this listing is not an exhaustive compilation of the various classes of coupling agents known in the art but, rather, is representative of the more common coupling agents.

In one embodiment, the topiramate analog can have L-X—Y selected from the group consisting of NHCO(CH$_2$)$_2$CONH(CH$_2$)$_2$NHCOOH, NHCO(CH$_2$)$_2$CONH(CH$_2$)$_2$NH-COONS, NHCO(CH$_2$)$_2$CONH(CH$_2$)$_2$NHCOOH$_2$CH$_3$, NHCO(CH$_2$)$_2$CONH(CH$_2$)$_2$NHCO(CH$_2$)$_2$COOH, NHCO(CH$_2$)$_2$CONH(CH$_2$)$_2$NHCO(CH$_2$)$_2$COONHS, NHCO(CH$_2$)$_2$ CONH(CH$_2$)$_2$NHCO(CH$_2$)$_2$COOCH$_2$CH$_3$, NHCO(CH$_2$)$_2$ CONH(CH$_2$)$_2$NHCO(CH$_2$)$_2$COOH, NHCO(CH$_2$)$_2$CONH(CH$_2$)$_2$NHCO(CH$_2$)$_3$COONHS, NHCO(CH$_2$)$_2$CONH(CH$_2$)$_2$ NHCO(CH$_2$)$_3$COOCH$_2$CH$_3$, NHCO(CH$_2$)$_2$CONH(CH$_2$)$_2$ NHCO(CH$_2$)$_6$COOH, NHCO(CH$_2$)$_2$CONH(CH$_2$)$_2$NHCO(CH$_2$)$_6$COONHS, NHCO(CH$_2$)$_2$CONH(CH$_2$)$_2$ NHCO(CH$_2$)$_6$ COOCH$_2$CH$_3$, NHCO(CH$_2$)$_2$CONH(CH$_2$)$_2$ NHCH$_2$PhCOOH, NHCO(CH$_2$)$_2$CONH(CH$_2$)$_2$NHCH$_2$PhCOONHS, NHCO(CH$_2$)$_2$CONH(CH$_2$)$_2$NHCH$_2$PhCOOCH$_2$CH$_3$, NHCO(CH$_2$)$_2$CONH(CH$_2$)$_2$NHCONH(CH$_2$)$_3$COOH, NHCO(CH$_2$)$_2$CONH(CH$_2$)$_2$HCONH(CH$_2$)$_3$COONHS, NHCO(CH$_2$)$_2$CONH(CH$_2$)$_2$ NHCONH(CH$_2$)$_3$COOCH$_3$, NHCO(CH$_2$)$_2$CONHCH$_2$PhCOOH, NHCO(CH$_2$)$_2$CONHCH$_2$PhCOOCH$_2$CH$_3$, NHCO(CH$_2$)$_2$COOH, NHCO(CH$_2$)$_2$COONHS, NHCO(CH$_2$)$_2$COOCH$_2$CH$_3$, NHCO(CH$_2$)$_3$COOH, NHCO(CH$_2$)$_3$COONHS, NHCO(CH$_2$)$_3$COOCH$_2$CH$_3$, NH(CH$_2$)$_2$NHCO(CH$_2$)$_6$COOH, NH(CH$_2$)$_2$NHCO(CH$_2$)$_6$COONHS, NH(CH$_2$)$_2$NHCO(CH$_2$)$_6$COOCH$_2$CH$_3$, NH(CH$_2$)$_2$NH(CH$_2$)$_3$COOC(CH$_3$)$_3$, NH(CH$_2$)$_2$NH(CH$_2$)$_3$COOH, NH(CH$_2$)$_2$NH(CH$_2$)$_3$COONHS, NHCH$_2$PhCOOH, NHCH$_2$PhCOONHS, NHCOPhCOOH, NHCOPhCOONHS, OOCNH(CH$_2$)$_3$COOCH$_2$CH$_3$, OOCNH(CH$_2$)$_3$COOCH$_3$, OOCNH(CH$_2$)$_3$OONHS, OOCNH(CH$_2$)$_3$COOH, NH(CH$_2$)$_3$COOH, NH(CH$_2$)$_3$COONHS, and the like.

In one embodiment, the topiramate analog can have L-X—Y-Z selected from the group consisting of NHCO(CH$_2$)$_2$CONH(CH$_2$)$_2$NHOO-BSA, NHCO(CH$_2$)$_2$CONH(CH$_2$)$_2$NHCO(CH$_2$)$_2$COO-BSA, NHCO(CH$_2$)$_2$CONH(CH$_2$)$_2$NHCO(CH$_2$)$_3$COO-BSA, NHCO(CH$_2$)$_2$CONH(CH$_2$)$_2$NHCO(CH$_2$)$_6$COO-BSA, NHCO(CH$_2$)$_2$CONH(CH$_2$)$_2$NHCH$_2$PhCOO-BSA, NHCO(CH$_2$)$_2$CONH(CH$_2$)$_2$NHCONH(CH$_2$)$_3$COO-BSA, NHCO(CH$_2$)$_2$CONHCH$_2$PhCOO-BSA, NHCO(CH$_2$)$_2$COO-BSA, NHCO(CH$_2$)$_3$COO-BSA, NH(CH$_2$)$_2$NHCO(CH$_2$)$_6$COO-BSA, NH(CH$_2$)$_2$NH(CH$_2$)$_3$COO-BSA, NHCH$_2$PhCOO-BSA, NHCOPhCOO-BSA, OOCNH(CH$_2$)$_3$COO-BSA, NH(CH$_2$)$_3$ COO-BSA, and the like.

In one embodiment, the topiramate analogs of Formulas 1A, 1B, 2A and/or 2B can be used as therapeutic agents. As such, the topiramate analogs can be used as anti-epileptic drugs similarly as topiramate. However, when a topiramate analog is used as a therapeutic agent, Z is preferably nothing so as to not form an immunogen. Thus, the non-immunogenic analogs of topiramate can be used in anti-epileptic regimens for animals, including humans.

II. Topiramate Immunogens

Implementing an immunoassay for the detection of a small molecule, such as topiramate, can be a challenge. This is because such small molecules can often lack antigenicity, which makes it difficult to generate antibodies against topiramate, and is particularly problematic with topiramate, which lacks immunogenicity. To increase the immunogenicity, larger antigenic compounds, including but not limited to bovine serum albumin, ovalbumin, keyhole limpet hemocyanin, and the like, can be coupled to the drug. Further, detection of the drug in an immunoassay generally requires the use of a detectable tracer conjugated to an antibody, topiramate, or topiramate analog.

Accordingly, coupling an operative group to topiramate at the sulfamate moiety or the 9-carbon methyl group can provide a topiramate immunogen that is sufficiently immunologically similar to topiramate so that antibodies induced by the immunogen can react with the immunogen, topiramate, and other topiramate analogs. As such, an immunogen based on topiramate is also considered a topiramate analog. Topiramate analogs in accordance with the present invention which include an immunogenic carrier can be capable of inducing the production of anti-topiramate antibodies, such as monoclonal and polyclonal antibodies. Accordingly, the antibodies generated using unique topiramate immunogens can interact and/or bind with topiramate and other topiramate analogs. These antibodies, immunogens, antigens, and analogs can be useful in preparing for and performing immunoassays for the detection of topiramate in biological samples.

Immunogens can be made by coupling topiramate to an antigenic carrier protein through a linker reacted with one of the functional groups of a topiramate derivative. A topiramate immunogen, which was based on a topiramate analog, was described in U.S. Pat. No. 5,952,187, which is incorporated herein by reference. However, the topiramate analogs were prepared with un-optimized chemistry, and did not produce optimal analogs, immunogens, or antibodies for use in commercialized topiramate detection applications. Thus, the analogs and immunogens prepared in accordance with the present invention have improved chemistry, linkers, and result in immunogens that can produce antibodies at titers sufficient for use in commercial applications.

In one embodiment, in order to increase the immunogenicity of a topiramate analog, a large antigenic compound, such as, keyhole limpet hemocyanin, can be coupled to a topiramate analog. Also, it has been found in some instances that longer linkers can increase the affinity of the antibodies produced. In part, it is thought, without being bound thereto, that longer linkers can allow more accessibility to the antigen. Also, due to the increased surface area of the exposed antigen or epitope, the avidity may also be increased, which may provide an improvement in the art.

In one embodiment, the present invention relates to immunogens prepared from the forgoing topiramate analogs. Namely, the analogs of Formulas 1B and 2B can include the linker moieties as described above, and Z can be an immunogen. As such, Z can be any immunogenic moiety that can elicit an immunological response and provide for antibodies to be produced that target at least a portion of the topiramate analog.

An immunogenic moiety can include various proteins or polypeptides, which can function as an immunogenic carrier. These types of polypeptides include albumins, serum proteins, globulins, ocular lens proteins, lipoproteins, and portions thereof. Illustrative proteins include bovine serum albumin ("BSA"), keyhole limpet hemocyanin ("KLH"), egg ovalbumin, bovine gamma-globulin ("BGG"), and the like. Alternatively, synthetic polypeptides may be utilized. Additionally, an immunogenic moiety can also be a polysaccharide, which is a high molecular weight polymer. Examples of polysaccharides are starches, glycogen, cellulose, carbohydrate gums such as gum arabic, agar, and the like. Also, an immunogenic moiety can be a polynucleotide, such as DNA or RNA. The polynucleotide can be modified or unmodified, and comprised of any number of nucleic acids so long as it provides the carrier and/or immunogenic functionality. The polysaccharide can also contain or link to a polypeptide residue, polynucleotide residue, and/or lipid residues. Furthermore, an immunogenic moiety can also be a polynucleotide either alone or conjugate to one of the polypeptides or polysaccharides mentioned above.

An immunogenic moiety or carrier can also be a particle or microparticle. The immunogenic particles are generally at least about 0.02 microns ($\mu$m) and not more than about 100 $\mu$m, and usually about 0.05 $\mu$m to 10 $\mu$m in diameter. The particle can be organic or inorganic, swellable or non-swellable, and/or porous or non-porous. Optionally, an immunogenic particle can have a density approximating water, generally from about 0.5 to 1.5 g/ml, and be composed of a material that can be transparent, partially transparent, or opaque. The immunogenic particles can be biological materials such as cells and microorganisms, including non-limiting examples such as erythrocytes, leukocytes, lymphocytes, *Streptococcus, Staphylococcus aureus, E. coli*, and viral particles. The particles can also be comprised of organic and inorganic polymers, liposomes, latex, phospholipid vesicles, liposomes, cationic liposomes, anionic liposomes, lipoproteins, lipopolymers, and the like.

In one embodiment, the topiramate analog can have L-X—Y-Z selected from the group consisting of $NHCO(CH_2)_2CONH(CH_2)_2NHCOO$-KLH, $NHCO(CH_2)_2CONH(CH_2)_2NHCO(CH_2)_2COO$-KLH, $NHCO(CH_2)_2CONH(CH_2)_2NHCO(CH_2)_3COO$-KLH, $NHCO(CH_2)_2CONH(CH_2)_2NHCO(CH_2)_6COO$-KLH, $NHCO(CH_2)_2CONH(CH_2)_2NHCH_2PhCOO$-KLH, $NHCO(CH_2)_2CONH(CH_2)_2NHCONH(CH_2)_3COO$-KLH, $NHCO(CH_2)_2CONHCH_2PhCOO$-KLH, $NHCO(CH_2)_2COO$-KLH, $NHCO(CH_2)_3COO$-KLH, $NH(CH_2)_2NHCO(CH_2)_6COO$-KLH, $NH(CH_2)_2NH(CH_2)_3COO$-KLH, $NHCH_2PhCOO$-KLH, $NHCOPhCOO$-KLH, $OOCNH(CH_2)_3COO$-KLH, $NH(CH_2)_3COO$-KLH, and the like.

Thus, the immunogens prepared in accordance with the present invention can be used to generate antibodies that can have an affinity for topiramate as well as topiramate analogs.

III. Antibodies for Topiramate and Topiramate Analogs

In one embodiment, a topiramate analog-based immunogen in accordance with the present invention can be used in an embodiment of a method for producing monoclonal and/or polyclonal antibodies. As such, antibodies can be produced from the topiramate-based immunogen and interact and/or bind with topiramate. This can allow for the analogs of the present invention to be useful in preparing antibodies for use in immunoassays for identifying the presence of topiramate.

Also, methods of producing antibodies with immunogens are well known in the art. The immunogens can be used in the screening for the monoclonal and/or polyclonal antibodies that interact and/or bind with topiramate.

FIG. 1 is a flow diagram illustrating one embodiment of a method 10 for obtaining anti-topiramate antibodies, an immunogen based on a topiramate analog can be obtained (Block 12). The immunogen can then be combined with an immunogenic formulation (Block 14). Briefly, about 0.5 mL of an immunogen composition is admixed with about 0.5 mL of complete Freund's adjuvant; however, other amounts of immunogen and/or adjuvant can be used. The immunogenic formulation can then be administered to an antibody producing subject (Block 16), which can be a rat, mouse, pig, rabbit, bird, sheep, and/or other animal, but preferably mammals. The administration can be via tail vein injection, subcutaneous injection, intravenous injection, or other well-known injection sites. Subsequently, immunogenic boosters can be administered to the animal that received the initial administration (Block 18), wherein the booster can include substantially the same ingredients as the initial formulation and can be administered at predetermined intervals. For example, the initial administration can be followed by subsequent boosters once a week or at other longer or shorter intervals. After at least the initial administration, and optionally after subsequent boosters, the anti-topiramate antibodies produced by the animal can be collected (Block 20). The antibodies can be collected by obtaining blood, serum, plasma, or other biological sample from the animal previously administered the immunogen. Optionally, the antibody-containing composition can then be processed as is well known in the art (Block 22), wherein such processing can include techniques that place the antibodies into a format suitable for performing an immunodiagnostic assay. Alternatively, the processing can include screening the antibodies with ELISA by well-known and established techniques. As such, the processing can be used to obtain polyclonal antibodies (Block 24), which can also result in purifying polyclonal antibodies (Block 26). Alternatively, techniques well known in the art can be used to obtain monoclonal antibodies, which can also result in purifying monoclonal antibodies.

IV. Immunodiagnostic Assays

The anti-topiramate antibodies, either monoclonal or polyclonal, can be used in immunoassays for identifying the presence of topiramate in a sample, such as blood, plasma, serum, tissue, and the like. This can be beneficial for identifying or determining pharmacokinetic and/or pharmacodynamic parameters for topiramate in a patient or patient population. Thus, the anti-topiramate antibodies can be used in immunodiagnostic assays in place of other antibodies so that the assays can be configured for identifying the presence and optionally quantifying the amount of topiramate. Additionally, the immunodiagnostic assays can use topiramate analogs in accordance with the present invention or other topiramate analogs.

A. Fluorescence Polarization Immunoassay for Topiramate

Fluorescence polarization immunoassay (FPIA) technology is based upon competitive binding between an antigen/drug in a sample and a known concentration of labeled antigen/drug. FPIA technology is described in U.S. Pat. Nos. 4,593,089, 4,492,762, 4,668,640, and 4,751,190, which are incorporated herein by reference. Accordingly, the FPIA reagents, systems, and equipment described in the incorporated references can be used with anti-topiramate antibodies which are also anti-topiramate analog antibodies.

The FPIA technology can be used to identify the presence of topiramate and can be used in assays that quantify the amount of topiramate in a sample. In part, the rotational properties of molecules in solution allow for the degree of polarization to be directly proportional to the size of the molecule. Accordingly, polarization increases as molecular size increases. That is, when linearly polarized light is used to excite a fluorescent-labeled or other luminescent-labeled topiramate or analog thereof, which is small and rotates rapidly in solution, the emitted light is significantly depolarized. When the fluorescent-labeled topiramate or analog interacts with or is bound to an antibody, the rotation is slowed and the emitted light is highly polarized. This is because the antibody significantly and measurably increases the size of the complex. Also, increasing the amount of unlabeled topiramate in the sample can result in decreased binding of the fluorescent-labeled topiramate or analog by the anti-topiramate antibody, and thereby decrease the polarization of light emitted from sample. The quantitative relationship between polarization and concentration of the unlabeled topiramate in the sample can be established by measuring the polarization values of calibrations with known concentrations of topiramate. Thus, FPIA can be used to identify the presence and concentration of topiramate in a sample.

One embodiment of the present invention is an FPIA assay system. An example of components of the FPIA system can include the following: i) monoclonal or polyclonal anti-topiramate antibodies capable of specifically binding to topiramate and a topiramate analog; ii) a sample suspected of containing the topiramate; and iii) topiramate analog labeled with a fluorescent moiety, such as fluorescein. Alternatively, the system can be provided as a kit exclusive of the sample. Additionally, the system can include various buffer compositions, topiramate concentration gradient compositions or a stock composition of topiramate, and the like.

Figure 2:
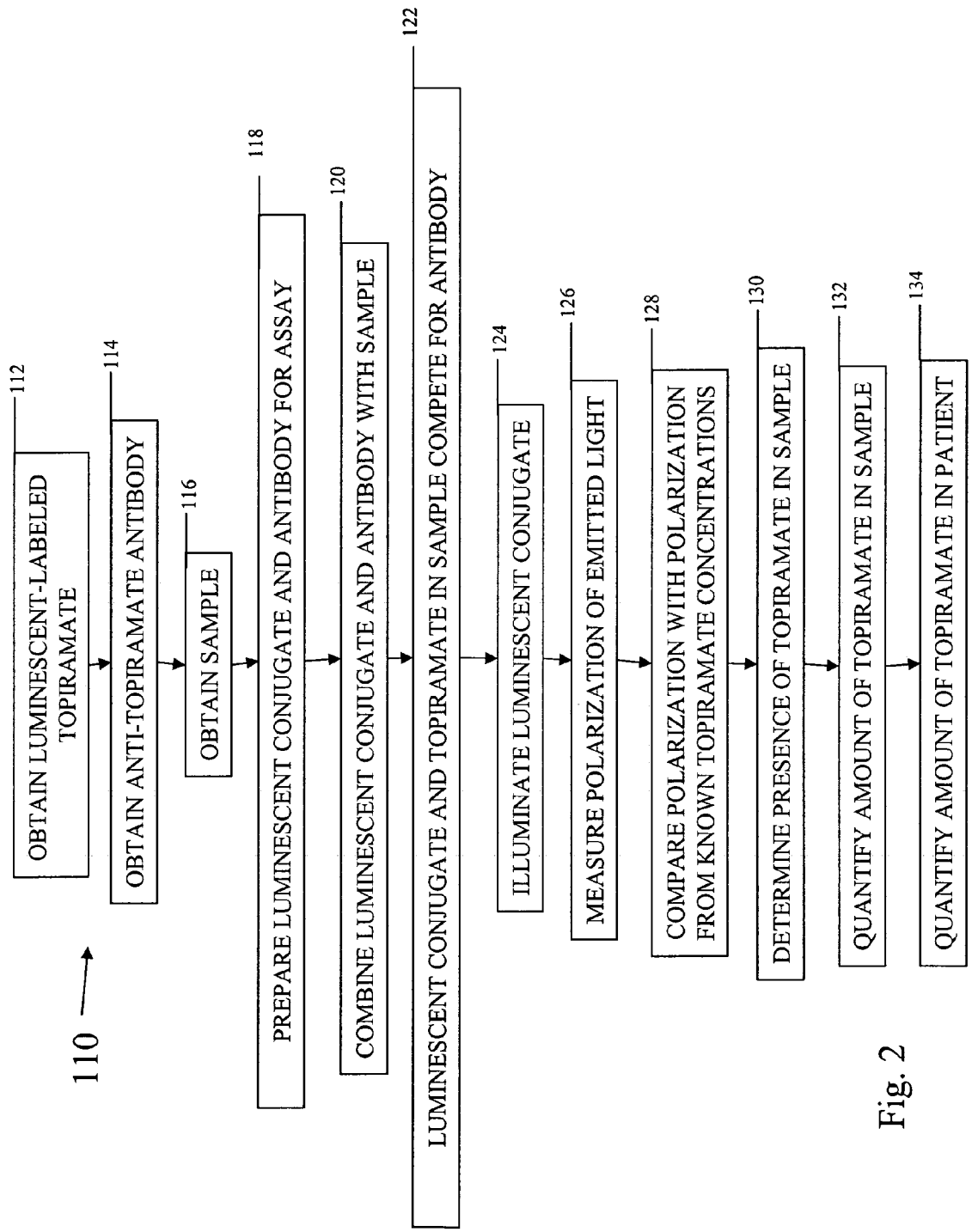
FIG. 2 is a flow diagram illustrating an embodiment of a method for performing an immunodiagnostic assay for topiramate.

FIG. 2 is a flow diagram illustrating one embodiment of a method 110 for performing a FPIA assay. As such, a luminescent-labeled topiramate or analog conjugate can be obtained (Block 112), and an anti-topiramate antibody can be obtained (Block 114). Additionally, a sample, such as a biological sample from a patient being administered topiramate, suspected of containing topiramate can be obtained (Block 116). Known amounts or concentrations of luminescent-labeled topiramate conjugate and anti-topiramate antibody can be obtained and formulated into separate compositions, such as in a standard buffer system, for use in a competitive binding assay (Block 118). The anti-topiramate antibody and luminescent-labeled topiramate conjugate are then combined with the biological sample into a reaction solution (Block 120). A competitive reaction takes place between the luminescent-labeled topiramate conjugate and the unknown amount of topiramate in the biological sample with the anti-topiramate antibody in the reaction solution (Block 122). After adequate duration and/or competition the luminescent conjugate is illuminated (Block 124), which can be by photoillumination, chemical-illumination, temperature-illumination, and the like. The polarization of the light emitted by the illumination is then measured (Block 126) and compared to polarization values of known amounts of topiramate and/or luminescent conjugate (Block 128), which can be used to determine whether or not topiramate is present in the sample (Block 130). Additionally, comparing the measurements obtained from the biological sample with standardized measurements obtained from known concentration standards can be used to quantify the amount of topiramate in the sample (Block 132), and thereby identify the amount of topiramate in the patient (Block 134).

B. Homogeneous Microparticle Immunoassay for Topiramate

Homogeneous microparticles immunoassay ("HMI") technology, which can be referred to as immunoturbidimetric assays, is based on the agglutination of particles and compounds in solution. When particles and/or chemical compounds agglutinate, particle sizes can increase and increase the turbidity of a solution. Accordingly, anti-topiramate antibodies can be used with microparticles and topiramate analogs in order to assess the presence, and optionally the amount, of topiramate in a sample. HMI technologies can be advantageous because the immunoassays can be performed on blood, blood hemolysate, serum, plasma, tissue, and/or other samples. HMI assays can be configured to be performed with topiramate and/or an analog loaded onto a microparticle, or with an anti-topiramate antibody loaded onto a microparticle. The use of an analog loaded microparticle can be especially advantageous because of the ability to efficiently load the microparticle. In any event, HMI or immunoturbidimetric assays are well known in the art for measuring agglutination of substances in a sample.

Immunoturbidimetric assay technologies are described in U.S. Pat. Nos. 5,571,728, 4,847,209, 6,514,770, and 6,248,597, which are included herein by reference. Briefly, in homogeneous assay methods use is made predominantly of light attenuation, nephelometric, or turbidimetric methods. The formation of an agglutinated compound AB from topiramate (A) and anti-topiramate antibody microparticle binding partner (B) can be measured by the change which occurs in the scattering or absorption of the incident light directed into the sample. Alternatively, the anti-topiramate antibody (A) can bind with a topiramate or analog loaded microparticle. When suspendable particles having an immobilized binding partner are used, there is an enhancement of the effects, which makes it possible to determine considerably lower topiramate concentrations. These homogeneous methods can be carried out quickly and simply, and permit, in particular, the automation of sample analyses as described in more detail below.

For example, in high volume screening applications it can be desirable to have fully automated methods of analysis. As such, instruments can be designed to detect changes in light scattering by particles, such as sensitized latex particles, as a result of specific reaction with analyte. The assays that utilize such instruments can be made highly sensitive due to the vast surface area of latex particle suspensions and the physical principles of light scattering. The main principle of detection involves the light scattering change when two or more particles come into close contact during agglutination. When a beam of light is passed through a reaction cell containing un-agglutinated particles, there can be a certain degree of light scatter due to refraction, reflection, absorption, and diffraction by the particles. Accordingly, this principle can be beneficial for measuring the ability of a target analyte, such as topiramate to inhibit agglutination of particles. During the early stages of antibody/antigen binding, complexes begin to form, wherein these complexes can substantially alter the angular distribution of the scattered light intensity because the complexes act like larger particles. The change of light scatter as a result of larger particles by agglutination may be measured by turbidimetric detection and other methods, as described in more detail below. Seradyn's topiramate QMS® reagents permit the complete automation and are applicable to many clinical chemistry analyzers.

Figure 3:
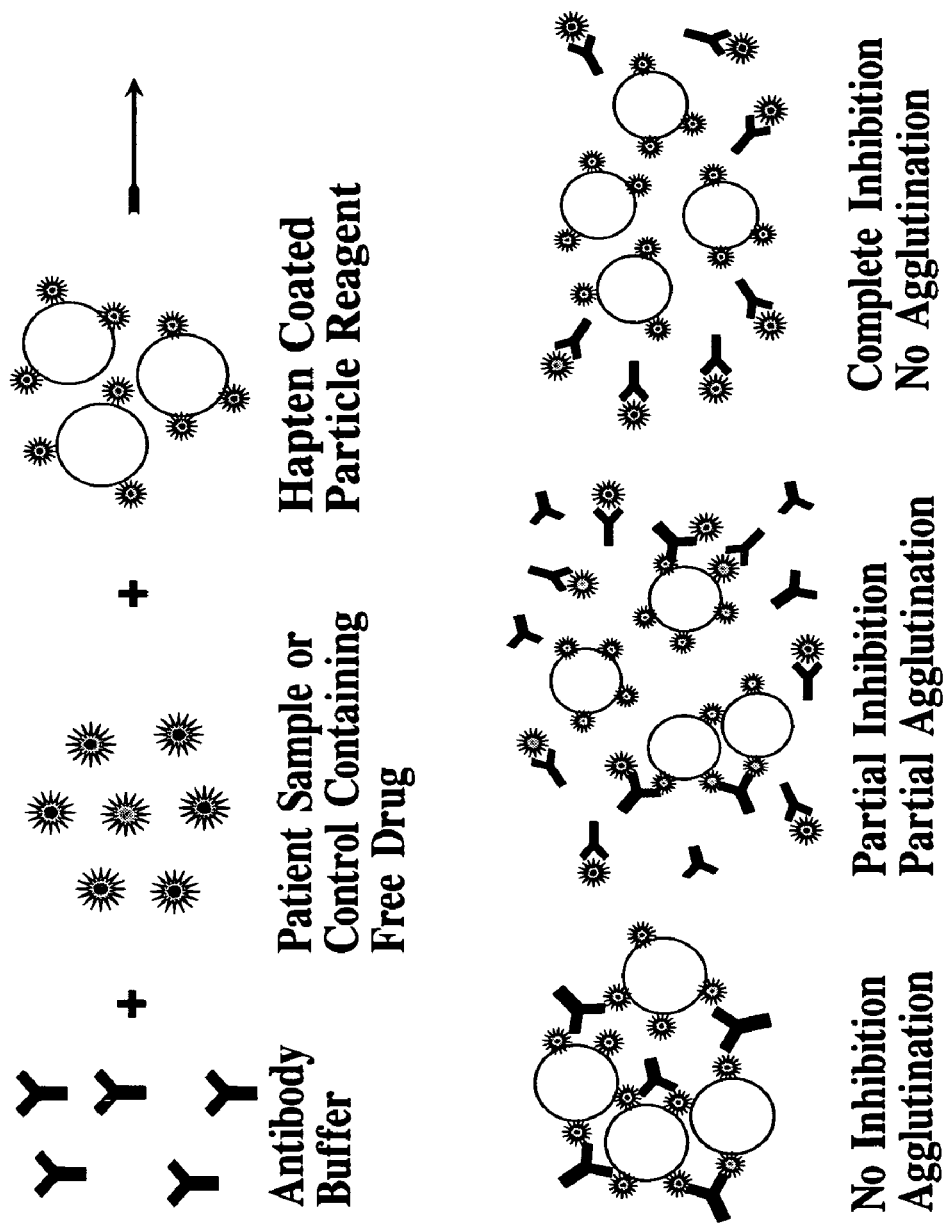
FIG. 3 is a schematic diagram illustrating an embodiment of a competitive binding study based on fluorescent polarization.
Figure 4:
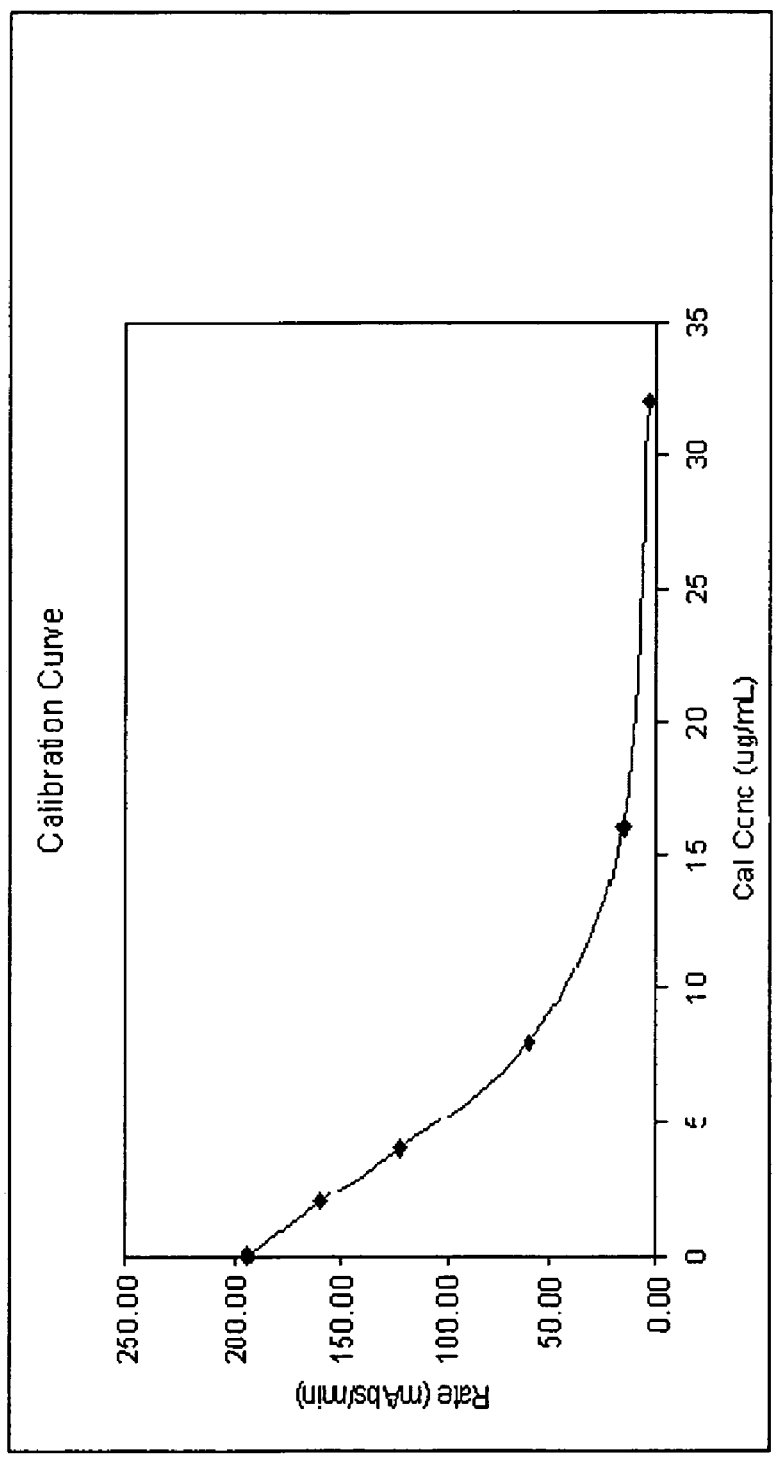
FIG. 4 is a graph illustrating an embodiment of a calibration curve for topiramate.

FIG. 3 is an illustration of a competition assay that combines an antibody buffer with a biological sample having a free drug, such as topiramate, and a hapten coated particle reagent, wherein the hapten can be a topiramate analog. In the instance the biological sample contains little or no topiramate, there is no inhibition of agglutination. As the amount of topiramate in the sample increases, there can be partial inhibition so as to result in only partial agglutination. Additionally, a large amount of topiramate in the sample can result in the complete inhibition of agglutination. Thus, the analysis of agglutination can be used to identify the presence of topiramate. Also, the use of a standardized curve of topiramate concentrations, as shown in FIG. 4, can be used to identify the amount of topiramate in the sample based on the absorbance change from agglutination.

i. Topiramate Loaded Microparticles

Figure 5:
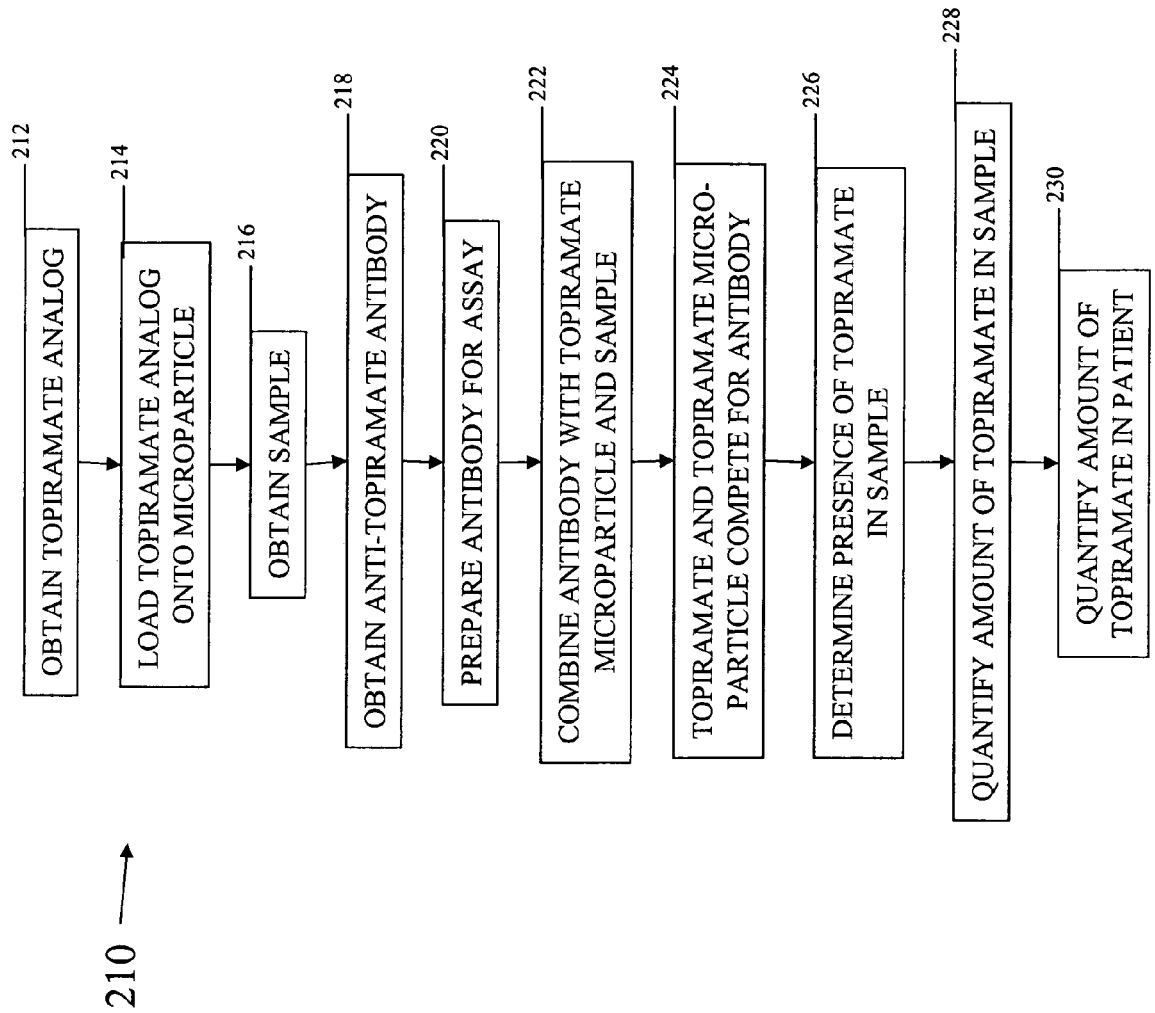
FIG. 5 is flow diagram illustrating an embodiment of a competitive binding study based on agglutination.

FIG. 5 is a flow diagram illustrating one embodiment of a method 210 for performing an HMI assay. Accordingly, topiramate analogs can be obtained (Block 212) and loaded on a microparticle (Block 214), such as any of the microparticles manufactured and/or sold by Seradyn, Inc. (Indianapolis, Ind.), which can include polystyrene, carboxylate-modified polystyrene, streptavidin-coated magnetic particles, and the like. A sample, such as a biological sample from a patient being administered topiramate, suspected of containing topiramate can be obtained (Block 216). An anti-topiramate antibody, such as monoclonal or polyclonal, capable of binding topiramate and topiramate analogs in accordance with the present invention is obtained (Block 218), and then optionally formulated in a standard buffer system (Block 220). The antibody composition is then combined with the topiramate-microparticle and biological sample (Block 222), wherein the amounts of antibody and topiramate analog bound to the microparticle are known. A competitive reaction takes place between the topiramate analog immobilized on the microparticles and the topiramate in the biological sample for binding to a limited amount of anti-topiramate antibody in the reaction solution (Block 224). Agglutination of topiramate-loaded microparticles with antibody is inhibited by the presence of topiramate in the biological sample, wherein agglutination inhibition is directly proportional to concentration of topiramate in the biological sample. This allows for the presence of topiramate in the sample to be determined by well-known turbidimetric assays (Block 226). Additionally, comparing the measurements obtained from the biological sample with standardized measurements obtained from known concentration standards can be used to quantify the amount of topiramate in the sample (Block 228), and thereby identify the amount of topiramate in the patient (Block 230).

One embodiment of the present invention is a topiramate analog-loaded microparticle HMI assay system. An example of components of the HMI system can include the following: i) monoclonal or polyclonal anti-topiramate antibodies capable of specifically binding to topiramate and a topiramate analog; ii) a sample suspected of containing the topiramate; and iii) topiramate analog coupled to a microparticle, such as a polystyrene microparticle. Alternatively, the system can be provided as a kit without the sample. Additionally, the system can include various buffer compositions, topiramate concentration gradient compositions or a stock composition of topiramate, and the like.

ii. Anti-Topiramate Antibody Loaded Microparticles

In another embodiment, which is similar to that described above with respect to topiramate loaded microparticles, an anti-topiramate antibody capable of binding topiramate and a topiramate analog is loaded on the microparticle. The topiramate analog can include an operative group of choice, for example, bovine serum albumin, ovalbumin, dextran, and the like. A competitive reaction takes place between the topiramate analog and topiramate in the patient's sample for binding to the anti-topiramate antibody immobilized on the microparticle. Again, agglutination of microparticles is inhibited by the presence of topiramate in the patient sample.

Figure 6:
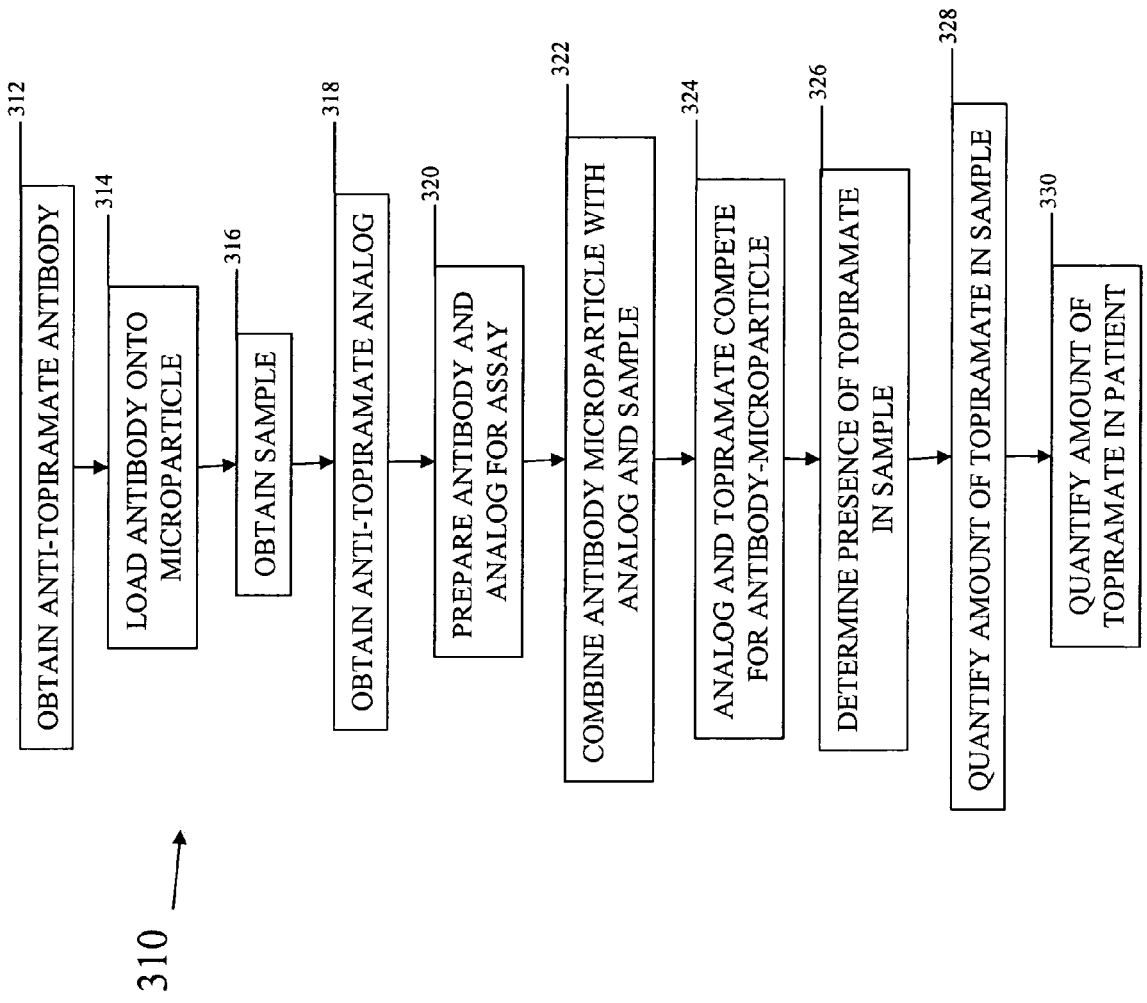
FIG. 6 is a flow diagram illustrating an embodiment of a competitive binding study based on agglutination.

FIG. 6 is a flow diagram illustrating another embodiment of a method 310 for performing an HMI assay. Accordingly, anti-topiramate antibodies capable of specifically binding topiramate and a topiramate analog can be obtained (Block 312) and loaded on a microparticle (Block 314). A sample, such as a biological sample from a patient being administered topiramate, suspected of containing topiramate can be obtained (Block 316). A topiramate analog can be obtained, where the analog can include a suitable operating group (Block 318). Known amounts or concentrations of the topiramate analog and anti-topiramate antibody-loaded microparticles are then formulated into separate compositions, such as a standard buffer system, for use in a competitive binding assay (Block 320). The antibody-microparticle composition is then combined with the topiramate analog composition and biological sample (Block 322). A competitive reaction takes place between the topiramate analog and topiramate in the biological sample for binding with the anti-topiramate antibody immobilized on the microparticle in the reaction solution (Block 324). Agglutination of the anti-topiramate antibody-loaded microparticles with the topiramate analog is inhibited by the presence of topiramate in the biological sample, wherein inhibition of agglutination is directly proportional to concentration of topiramate in the biological sample. This allows for the presence of topiramate in the sample to be determined by well-known turbidimetric assays (Block 326). Additionally, comparing the measurements obtained from the biological sample with standardized measurements obtained from known concentration standards can be used to quantify the amount of topiramate in the sample (Block 328), and thereby identify the amount of topiramate in the patient (Block 330)

One embodiment of the present invention is an anti-topiramate antibody loaded microparticle HMI assay system. An example of components of the HMI system can include the following: i) microparticles loaded with monoclonal or polyclonal anti-topiramate antibodies that are capable of binding to topiramate and a topiramate analog; ii) a sample suspected of containing the topiramate; and iii) a topiramate analog, which can optionally include an operative group. Alternatively, the assay system can be provided as a kit exclusive of the sample. Additionally, the assay system can include various buffer compositions, topiramate concentration gradient compositions or a stock composition of topiramate or analog, and the like.

C. Cloned Enzyme Donor Immunoassays for Topiramate

Cloned enzyme donor Immunoassays ("CEDIA®" a trademark of Roche Diagnostics) has proven to be a highly accurate and effective method for identifying the presence and determining the amount of therapeutic drugs. The CEDIA® technology has been described in detail in the following patents: (a) U.S. Pat. No. 4,708,929 disclosing competitive homogeneous assay methods; (b) U.S. Pat. No. 5,120,653 disclosing a recombinant DNA sequence for coding the enzyme donor fragment and a host for such a vector; (c) U.S. Pat. No. 5,604,091 disclosing amino acid sequences of the enzyme donor fragment; and (d) U.S. Pat. No. 5,643,734 which teaches kits for CEDIA assays, wherein all of the foregoing patents are incorporated herein by reference. Briefly, CEDIA® technology is based upon the competition of topiramate in the biological sample with an analog coupled to an inactive genetically engineered enzyme-donor ("ED") fragment such as from β-D-galactoside galactohydrolase or β-galactosidase ("β gal") from *E. coli*, for binding to an antibody capable of binding topiramate. In the instance the topiramate is present in the sample it binds to the antibody, leaving the ED portion of the ED-analog conjugate free to restore enzyme activity of β-D-galactoside galactohydrolase or β gal in the reaction mixture so as to be capable of association with enzyme acceptor ("EA") fragments. The active enzyme comprised of the ED and EA is then capable of producing a quantifiable reaction product when exposed to an appropriate substrate. A preferred substrate is chlorophenol red-β-D-galactopyranoside ("CPRG"), which can be cleaved by the active enzyme into galactose and CPR, wherein CPR is measured by absorbency at about wavelength 570 nm. In the instance topiramate is not present in the sample, the antibody binds to the ED-analog conjugate, thereby inhibiting association of the ED fragments with the EA fragments and inhibiting restoration of enzyme activity. The amount of reaction product and resultant absorbance change are proportional to the amount of topiramate in the sample.

Figure 7:
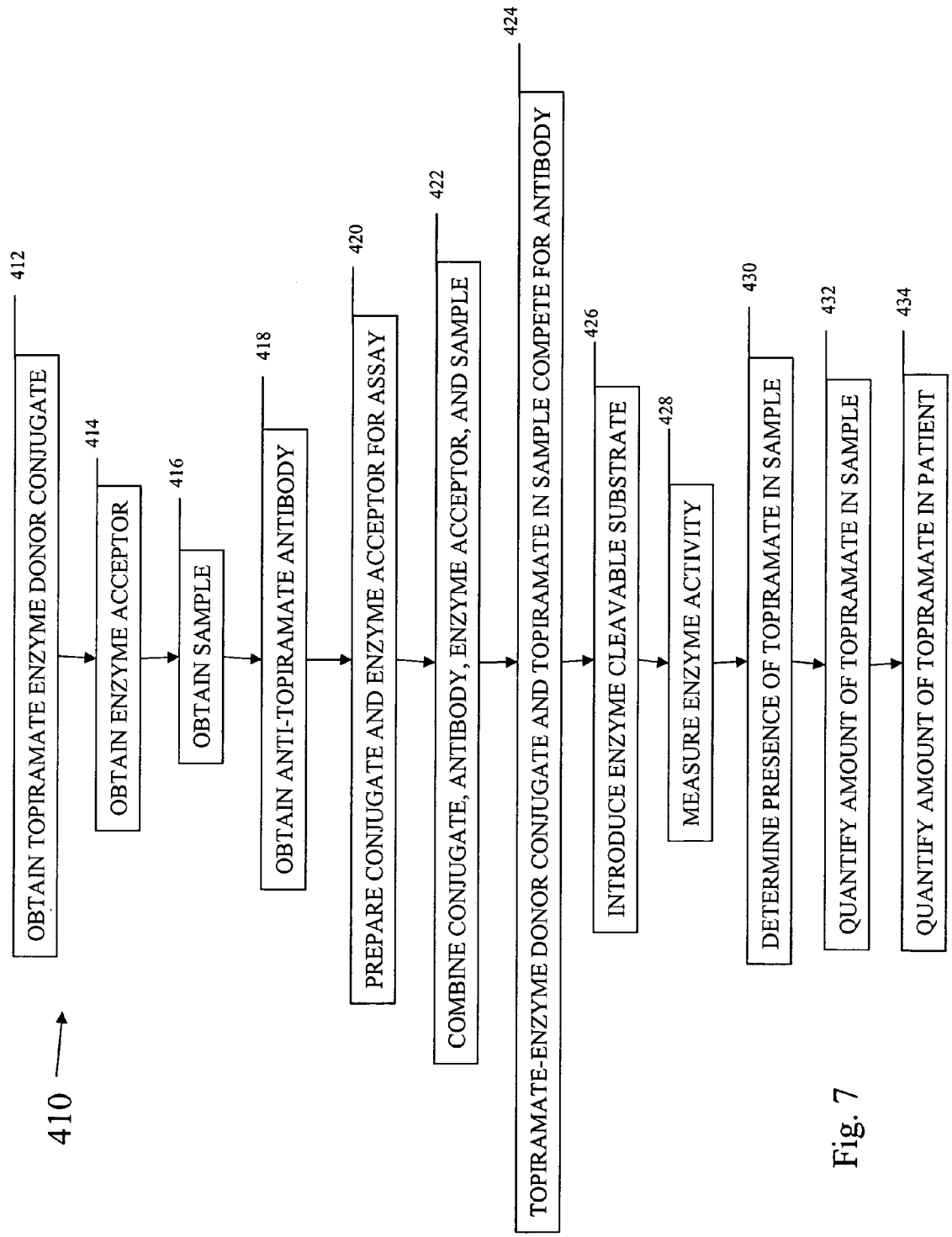
FIG. 7 is a flow diagram illustrating an embodiment of a competitive binding study based on enzymatic activity.

FIG. 7 is a flow diagram illustrating one embodiment of a method 410 for performing a CEDIA® assay. Accordingly, a topiramate-ED conjugate can be obtained (Block 412), which can be by coupling a topiramate analog with the ED. Also, an EA corresponding with the ED can be obtained (Block 414). Additionally, a sample, such as a biological sample from a patient being administered topiramate, suspected of containing topiramate can be obtained (Block 416). Anti-topiramate antibody, which can also interact with the topiramate-ED conjugate can be obtained by methods in accordance with the present invention (Block 418). Known amounts or concentrations of the topiramate-ED conjugate, EA, and anti-topiramate antibody are obtained and formulated into separate compositions, such as a standard buffer system, for use in a competitive binding assay (Block 420). The topiramate-ED conjugate and antibody is then combined with the biological sample into a reaction solution (Block 422). Optionally, the EA is also combined into the reaction solution at this point or later after a sufficient time for competitive interactions with the antibody to occur. A competitive reaction takes place between the known amount of topiramate-ED conjugate and topiramate in the biological sample with the known amount of anti-topiramate antibody in the reaction solution (Block 424). After the competitive reactions and the EA has been introduced into the reaction solution, an ED-EA enzyme-cleavable substrate is introduced into the reaction solution (Block 426). The enzyme activity between the ED-EA enzyme and enzyme-cleavable substrate is measured (Block 428), which can be by measuring the absorbance of a cleavage product or other well-known measuring technique. The measurement of enzyme activity can be used to determine whether or not topiramate is present in the sample (Block 430). Additionally, comparing the measurements obtained from the biological sample with standardized measurements obtained from known concentration standards can be used to quantify the amount of topiramate in the sample (Block 432), and thereby identify the amount of topiramate in the patient (Block 434).

One embodiment of the present invention is a CEDIA® assay system. An example of components of the CEDIA® system can include the following: i) monoclonal or polyclonal anti-topiramate antibodies capable of binding to topiramate, topiramate analog, and/or topiramate-ED or topiramate-EA; ii) a sample suspected of containing the topiramate; iii) topiramate analog coupled to an ED or EA; and iv) one of an ED or EA that will associate with the topiramate-ED or topiramate-EA for restoring enzymatic activity so that an ED and EA are present in the system. Alternatively, the assay system can be provided as a kit exclusive of the sample. Additionally, the assay system can include various buffer compositions, topiramate concentration gradient compositions or a stock composition of topiramate, and the like.

D. Chemiluminescent Heterogeneous Immunoassays for Topiramate

A competitive assay using chemiluminescent microparticle immunoassay ("CMIA") technology can also be used to assess whether or not topiramate is present in a sample. Various types of CMIA technologies are well known in the art of heterogeneous immunoassays for determining the presence and/or amount of a chemical entity in a sample. Some CMIA technologies can be exemplified by U.S. Pat. Nos. 6,448,091, 5,798,083, and 5,834,206, which are incorporated herein by reference. CMIA assays can include the use of anti-topiramate antibodies, which are capable of binding to topiramate and its analogs, which are coupled to particles, such as magnetic particles or particles suitable for separation by filtration, sedimentation, and/or other means. Additionally, a tracer, which can include a topiramate analog linked to a suitable chemiluminescent moiety, can be used to compete with free topiramate in the patient's sample for the limited amount of anti-topiramate antibody on the particle. After the sample, tracer, and antibody particles interact and a routine wash step has removed unbound tracer, the amount of tracer bound to antibody particles can be measured by chemiluminescence, wherein chemiluminescence is expressed in Relative Light Units (RULE). The amount of chemiluminescence is inversely related to the amount of free drug in the patient's sample and concentration is determined by constructing a standard curve using known values of the drug.

Figure 8:
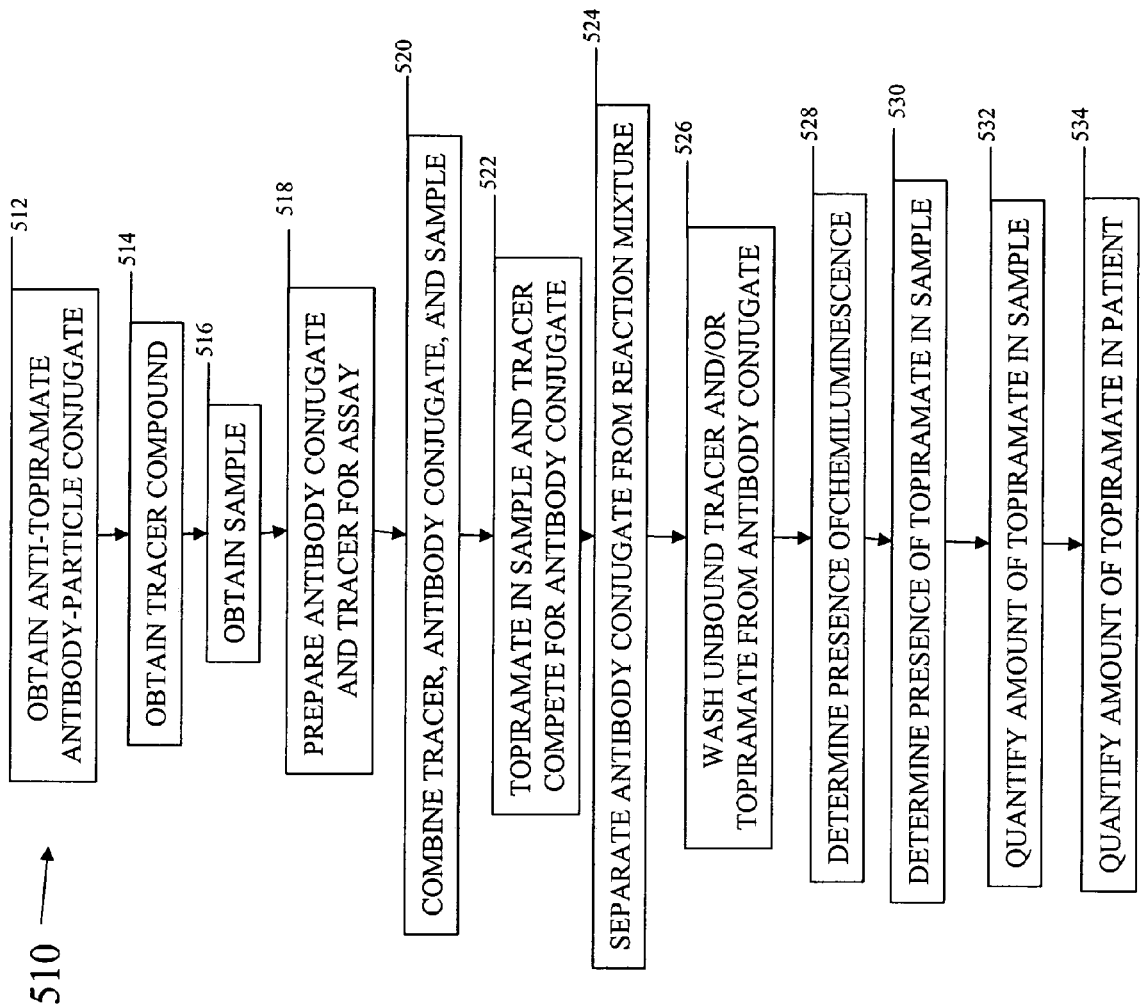
FIG. 8 is a flow diagram illustrating an embodiment of a competitive binding study based on chemiluminescence.

FIG. 8 is a flow diagram illustrating one embodiment of a method 510 for performing a CMIA assay. Accordingly, an anti-topiramate antibody-particle conjugate can be obtained (Block 512), which can be performed by coupling the antibody to a particle such as a magnetic particle. Also, a tracer compound including a topiramate analog having a chemiluminescent moiety can be obtained (Block 514). Additionally, a sample, such as a biological sample from a patient being administered topiramate, suspected of containing topiramate can be obtained (Block 516). Known amounts or concentrations of tracer and anti-topiramate antibody-particle conjugate can be formulated into separate compositions, such as a standard buffer system, for use in a competitive binding assay (Block 518). The anti-topiramate antibody-particle conjugate and tracer are then combined with the biological sample into a reaction solution (Block 520). A competitive reaction takes place between the tracer and topiramate in the biological sample for binding with the anti-topiramate antibody-particle conjugate in the reaction solution (Block 522). After sufficient duration and/or binding competition, the antibody-particle conjugate is separated from the reaction solution (Block 524). Optionally, any unbound topiramate and/or tracer can be removed from the antibody-particle conjugate by a wash or other separation technique (Block 526). The amount of chemiluminescence can be determined by exciting the tracer so that the chemiluminescent moiety emits light by phosphorescence, fluorescence, or other luminescence that is measurable (Block 528). Often, the chemiluminescence is fluorescence, which is measured in RLUs. The measurement of chemiluminescence can be used to determine whether or not topiramate is present in the sample (Block 530). Additionally, comparing measurements obtained from the biological sample with standardized measurements obtained from known concentration standards can be used to quantify the amount of topiramate in the sample (Block 532), and thereby identify the amount of topiramate in the patient (Block 534).

One embodiment of the present invention is a CMIA assay system. An example of components of the CMIA system can include the following: i) particles or microparticles loaded with monoclonal or polyclonal anti-topiramate antibodies that are capable of binding to topiramate and topiramate analog; ii) a sample suspected of containing the topiramate; and iii) an analog tracer. Alternatively, the assay system can be provided as a kit exclusive of the sample. Additionally, the system can include various buffer compositions, topiramate concentration gradient compositions or a stock composition of topiramate or analog, and the like.

E. Other Immunoassays for Topiramate

The topiramate analogs, conjugates, antibodies, immunogens and/or other conjugates described herein are also suitable for any of a number of other heterogeneous immunoassays with a range of detection systems including but not limited to enzymatic or fluorescent, and/or homogeneous immunoassays including but not limited to rapid lateral flow assays, and antibody arrays, as well as formats yet to be developed.

While various immunodiagnostic assays have been described herein that utilize the topiramate analogs, conjugates, antibodies, immunogens and/or tracers, such assays can also be modified as is well known in the art. As such, various modifications of steps or acts for performing such immunoassays can be made within the scope of the present invention.

EXAMPLES

The following examples are provided to illustrate embodiments of the prevention and are not intended to be limiting. Accordingly, some of the examples have been performed via experiment and some are prophetic based on techniques, standards, and results well known in the art. Also, it should be apparent that the invention can include additional embodiments not illustrated by example. Additionally, many of the examples have been performed with experimental protocols well known in the art using the topiramate analogs, antigens, immunogens, and anti-topiramate antibodies prepared in accordance with the present invention. Thus, the examples can be supplemented with the following references, which are all incorporated herein by reference: (a) Caryl Griffin et al., *Microparticle Reagent Optimization: A Laboratory Reference Manual from the Authority on Microparticles*, Seradyn (1994); (b) Boehringer Mannheim Corporation Technical Publications Department, *Hitachi Operation Manual: Version B*, Boehringer Mannheim Corporation Laboratory Diagnostic Division (1992); and (c) the NCCLS, approved guideline August 2004

Example 1

Figure 9:
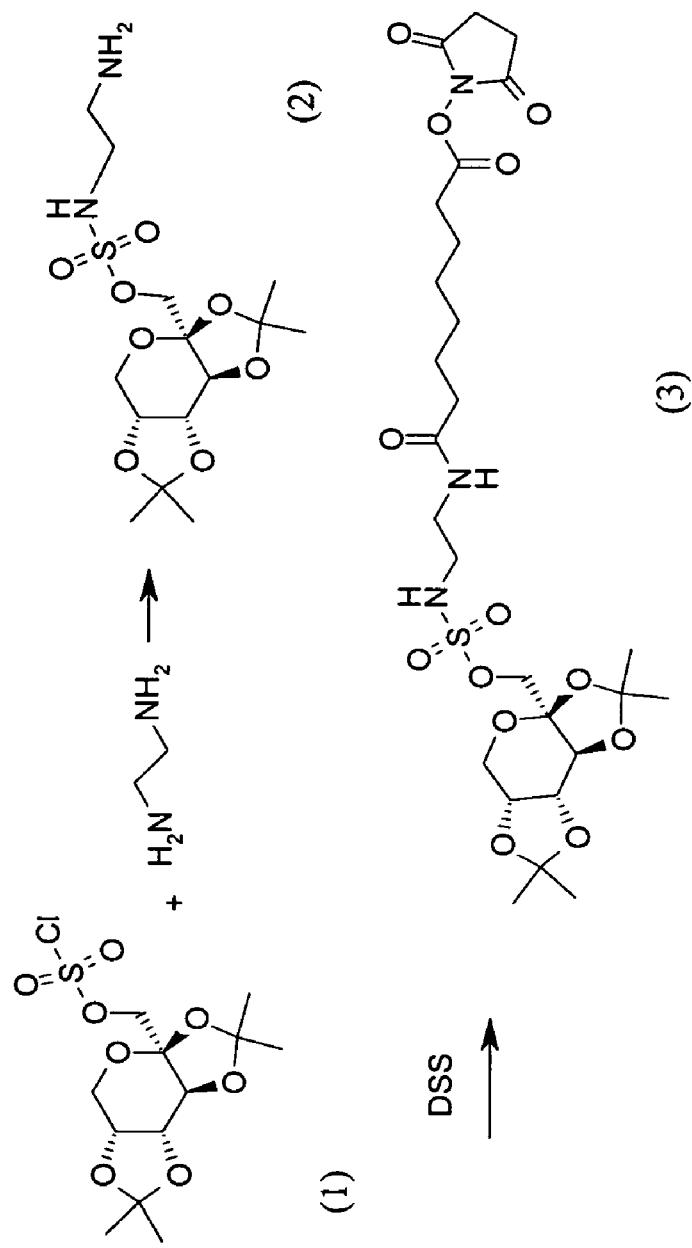
FIG. 9 is a schematic diagram illustrating an embodiment of a synthesis protocol for synthesizing a topiramate analog.

FIG. 9 is a schematic representation of a chemical reaction for converting topiramate chloride (1) into a sulfamate-conjugated aminoethyl-topiramate analog (2). In a round bottom flask, about 0.16 mL of an ethylenediamine solution is added to a solution of about 0.3 mL N,N-diisoproylethylamine and 0.5 mL DMF. The flask is chilled in an ice bath and stirred under argon ("Ar") gas before a solution of 203 mg of topiramate chloride in 1.0 mL DMF is added to form a reaction mixture. The reaction mixture is stirred under Ar gas for 12 h. The solvent is evaporated under reduced pressure to form a residue that is purified by flash column chromatography with a methanol eluent. The fractions containing an aminoethyl analog of topiramate (2) are combined and concentrated to yield about 90 mg.

Example 2

With continuing reference to FIG. 9, a schematic representation of a chemical reaction is depicted for converting the aminoethyl analog of topiramate (2) to another analog having a long linker and an active ester (3). In a round bottom flask which is in an ice bath, about 150 mg of DSS is added to a solution of 2 mL anhydrous DMF and 0.05 mL of N,N-diisopropylethylamine, which is then stirred under Ar. About 45 mg of the aminoethyl analog of topiramate (2) in 1 mL DMF (pre-chilled in an ice bath) is then added to the flask drop-wise to form a reaction mixture. The reaction mixture is stirred in an ice bath under Ar for 3 hours before the solvent is evaporated under reduced pressure to form a residue that is purified by flash column chromatography with an ethyl acetate hexane (8:2) eluant. The fractions containing the active ester of topiramate (3) are combined and concentrated to yield about 20 mg.

Example 3

Figure 10A:
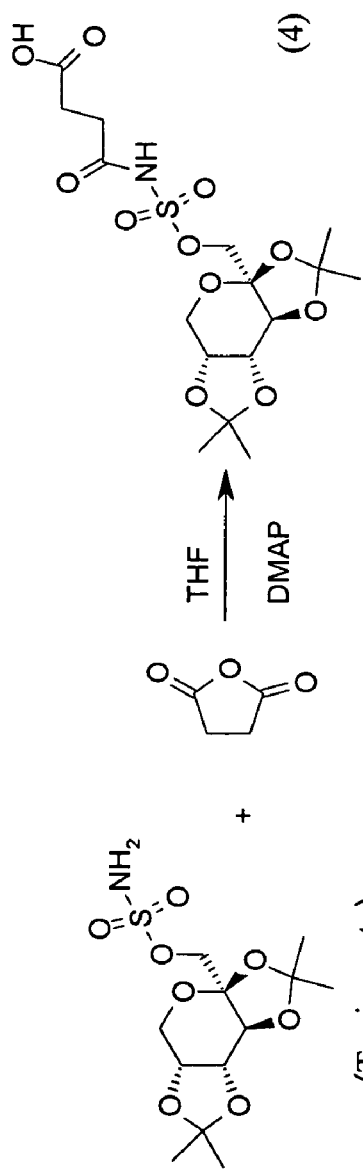
FIGS. 10A and 10B are schematic diagrams illustrating an embodiment of synthesis protocols for synthesizing topiramate analogs.

FIG. 10A is a schematic representation of a chemical reaction for converting topiramate into a sulfamate-conjugated succinyl analog of topiramate (4). In a 250 mL round bottom flask, a solution of about 2 g of topiramate in 20 mL THF (anhydrous) is combined with about 2 mL N,N-diisoproylethylamine, and stirred under Ar. About 1.24 g of succinic anhydride and 50 mg of DMAP are added to the above solution to form a reaction mixture. The reaction mixture is stirred under Ar for 12 hours, and the solvent is evaporated under reduced pressure to form a residue. The residue is purified by flash column chromatography with ethyl acetate as the eluent. The fractions containing the succinyl derivative of topiramate (4) are combined and concentrated to yield about 200 mg.

Example 4

Figure 10B:
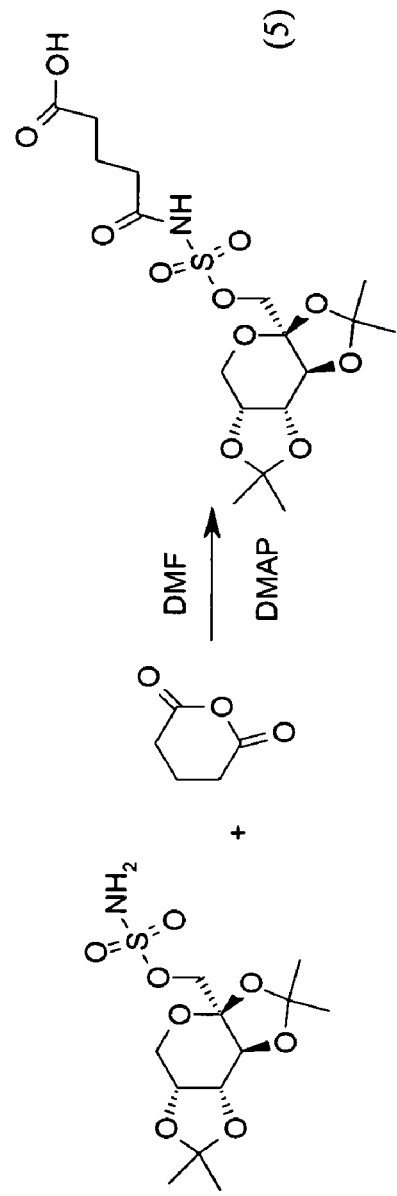

FIG. 10B is a schematic representation of a chemical reaction for converting topiramate into a sulfamate-conjugated glutaryl analog of topiramate (5). In a 250 mL round bottom flask, a solution of 400 mg of topiramate in 10 mL THF (anhydrous) is combined with 0.8 mL N,N-diisoproylethylamine, and stirred under Ar. About 520 mg of glutaric anhydride and 20 mg of DMAP are then added to form a reaction mixture. The reaction mixture is stirred at 60° C. for 60 hours, and the solvent is evaporated under reduced pressure to form a residue. The residue is purified by flash column chromatography with an ethyl acetate eluent. The fractions containing the glutaryl derivative of topiramate (5) are combined and concentrated to yield about 160 mg.

Example 5

Figure 11:
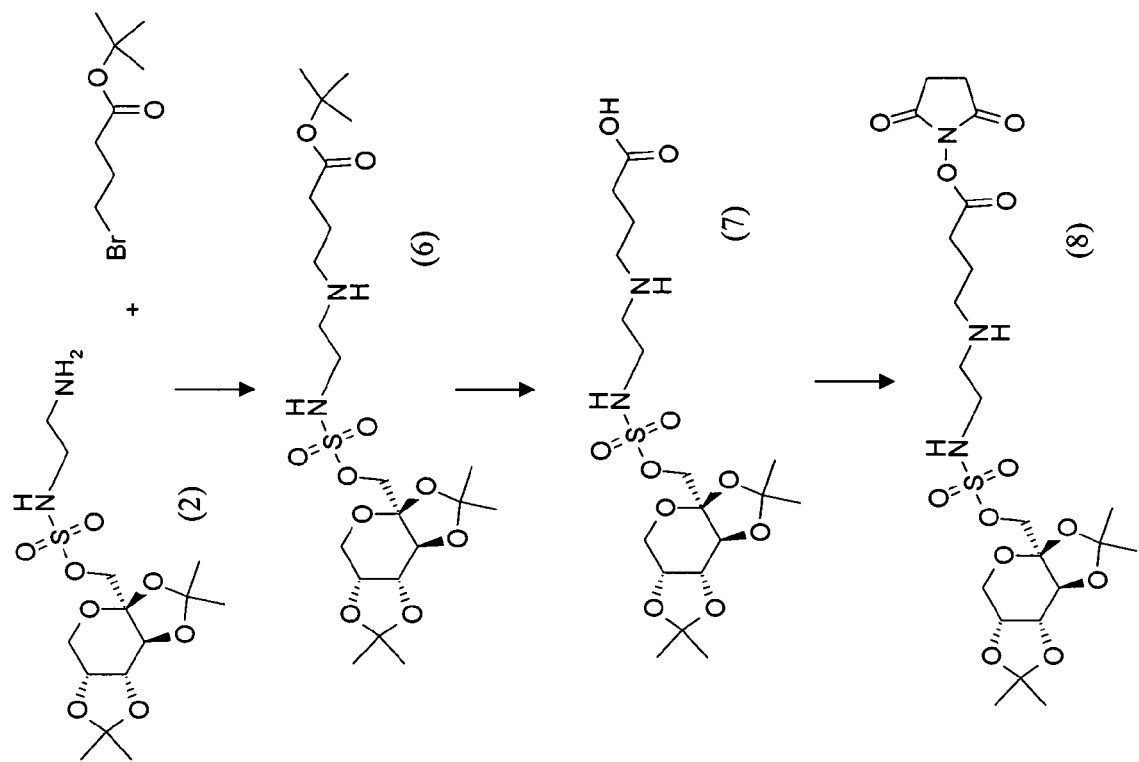
FIG. 11 is a schematic diagram illustrating an embodiment of a synthesis protocol for synthesizing a topiramate analog.

FIG. 11 is a schematic representation of a chemical reaction for converting the aminoethyl analog of topiramate (2) into a sulfamate-conjugated analog of topiramate (6) having an aliphatic ester group. In a 250 mL round bottom flask, a solution of 50 mg of aminoethyl topiramate (2) in 10 mL DMF (anhydrous) is combined with 0.8 mL N,N-diisoproylethylamine, and stirred under Ar. About 100 mg of t-butyl-4-bromobutyrate and 20 mg of DMAP are then added to form a reaction mixture. The reaction mixture is stirred at 80° C. for 24 hours, and the solvent is evaporated under reduced pressure to form a residue. The residue is purified by flash column chromatography with an ethyl acetate eluent. The fractions containing the sulfamate-conjugated analog of topiramate (6) are combined and concentrated to yield about 30 mg.

Example 6

With continuing reference to FIG. 11, a schematic representation is depicted of a chemical reaction for converting the sulfamate-conjugated analog of topiramate (6) into another sulfamate-conjugated analog of topiramate (7) having a carboxylic acid group. In a 250 mL round bottom flask, a solution of 50 mg of sulfamate-conjugated analog of topiramate (6) in 5 ml trifluoroacetic acid is combined with 5 mL of dichloromethane, and stirred under Ar. The reaction mixture is stirred at room temperature for 30 minutes, and the solvent is evaporated under reduced pressure to form a residue. The residue is purified by flash column chromatography with an ethyl acetate eluent. The fractions containing the sulfamate-conjugated analog of topiramate (7) are combined and concentrated to yield about 20 mg.

Example 7

With continuing reference to FIG. 11, a schematic representation is depicted of a chemical reaction for converting the sulfamate-conjugated analog of topiramate (7) into an activated ester of topiramate (8) having an active NHS group. Specifically, a solution of 100 mg of the topiramate analog (7) in 7 mL anhydrous DMF is cooled to 0° C., and 0.1 mL N,N-diisopropylethylamine is added to form a reaction mixture. The reaction mixture is reacted by the addition of 110 mg of O-(N-succinimidyl)-N,N,N',N'-tetramethyluronium tetrafluoroborate. The reaction mixture allowed to warm up to room temperature and stirred overnight. The reaction mixture is concentrated under reduced pressure, and the residue is purified by flash column chromatography using ethyl acetate/methanol as eluent to give approximately 60 mg of active ester of topiramate (8).

Example 8

Figure 12:
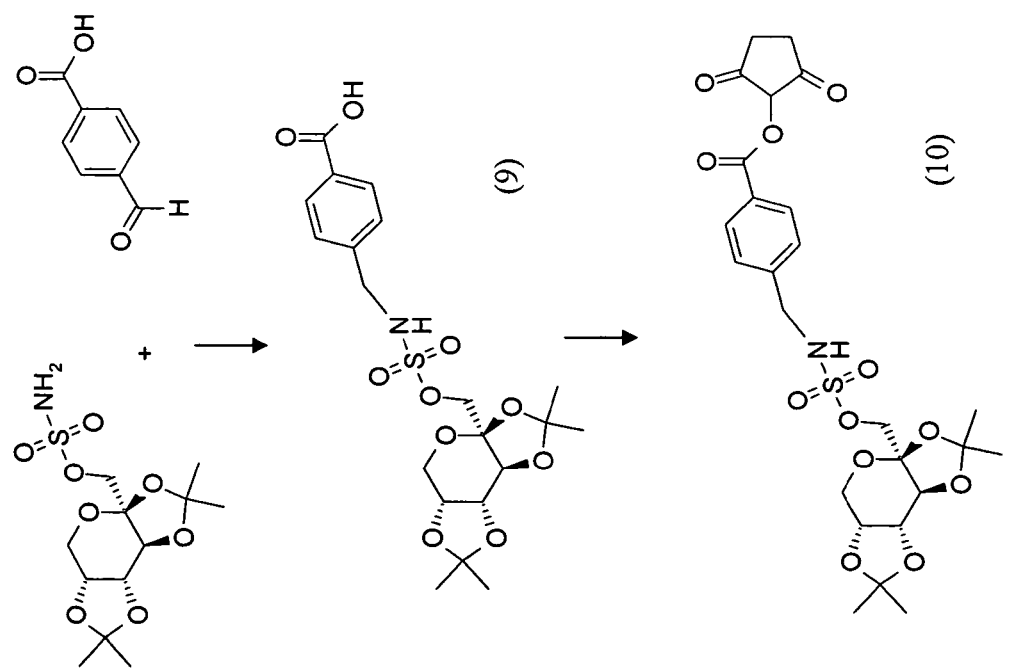
FIG. 12 is a schematic diagram illustrating an embodiment of a synthesis protocol for synthesizing a topiramate analog.

FIG. 12 is a schematic representation of a chemical reaction for converting topiramate into a sulfamate-conjugated phenyl analog of topiramate (9). In a 250 mL round bottom flask, a solution of 100 mg of topiramate in 10 mL dichloromethane is combined with 60 mg of 4-carboxybenzaldehyde and 40 mg sodium cyanoborohydride, and stirred under Ar. The reaction mixture is stirred at room temperature for 1 day. The reaction is quenched with water and extracted three times with 50 mL dicholomethane. The organic phases are combined and dried over anhydrous sodium sulfate, filtered, and the solvent removed on a rotary evaporator. The residue is purified by flash column chromatography with an ethyl acetate eluent. The fractions containing the phenyl analog of topiramate (9) are combined and concentrated to yield about 50 mg.

Example 9

With continuing reference to FIG. 12, a schematic representation of a chemical reaction is depicted for converting a phenyl analog of topiramate (9) into an activated NHS ester of the phenyl analog (10). Specifically, a solution of 90 mg of the phenyl analog of topiramate (9) in 5 mL anhydrous DMF is cooled to 0° C., and 0.1 mL N,N-diisopropylethylamine is added to form a reaction mixture. The reaction mixture is reacted by the addition of 95 mg of O-(N-succinimidyl)-N,N,N',N'-tetramethyluronium tetrafluoroborate. The reaction mixture is allowed to warm up to room temperature and stirred overnight. The reaction mixture is concentrated under reduced pressure, and the residue is purified by flash column chromatography using ethyl acetate/methanol as eluent to give approximately 50 mg of active ester of the phenyl analog (10).

Example 10

Figure 13:
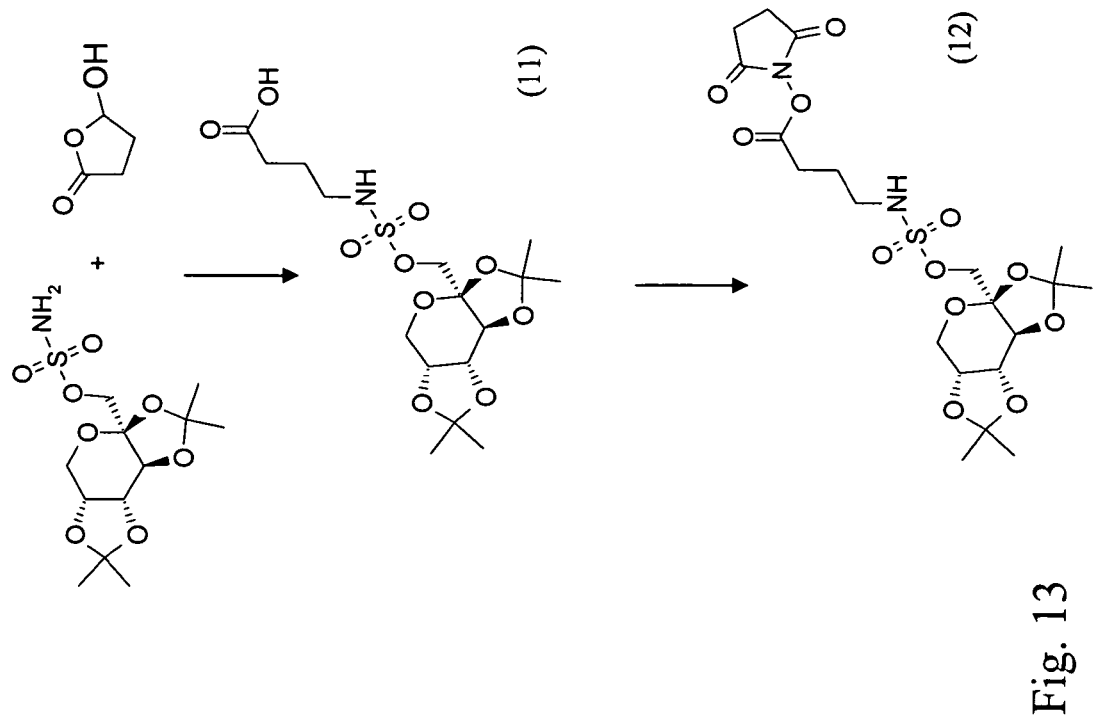
FIG. 13 is a schematic diagram illustrating an embodiment of a synthesis protocol for synthesizing a topiramate analog.

FIG. 13 is a schematic representation of a chemical reaction for converting topiramate into a sulfamate-conjugated butyric acid analog of topiramate (11). In a 250 mL round bottom flask, a solution of 400 mg of topiramate in 10 mL dichloromethane is combined with 100 mg sodium cyanoborohydride and 100 mg of succinic semialdehyde (15% by weight in water), and stirred at room temperature overnight. The reaction is quenched with 20 mL deionized water, acidified with 0.1 N HCl, and extracted three times with 40 mL of dichloromethane. The organic phases are combined and dried over anhydrous sodium sulfate, filtered, and the solvent removed on a rotary evaporator. The residue is purified by flash column chromatography with an ethyl acetate eluent. The fractions containing the butyric acid analog of topiramate (11) are combined and concentrated to yield about 160 mg.

Example 11

With continuing reference to FIG. 13, a schematic representation of a chemical reaction is depicted for converting butyric acid analog of topiramate (11) into an activated NHS ester of the butyric acid analog (12). Specifically, a solution of 100 mg of the butyric acid analog of topiramate (11) in 5 mL anhydrous DMF is cooled to 0° C., and 0.1 mL N,N-diisopropylethylamine is added to form a reaction mixture. The reaction mixture is reacted by the addition of 105 mg of O-(N-succinimidyl)-N,N,N',N'-tetramethyluronium tetrafluoroborate. The reaction mixture is allowed to warm up to room temperature and stirred overnight. The reaction mixture is concentrated under reduced pressure, and the residue is purified by flash column chromatography using ethyl acetate/methanol as eluent to give approximately 500 mg of active ester of the butyric acid analog (12).

Example 12

Figure 14:
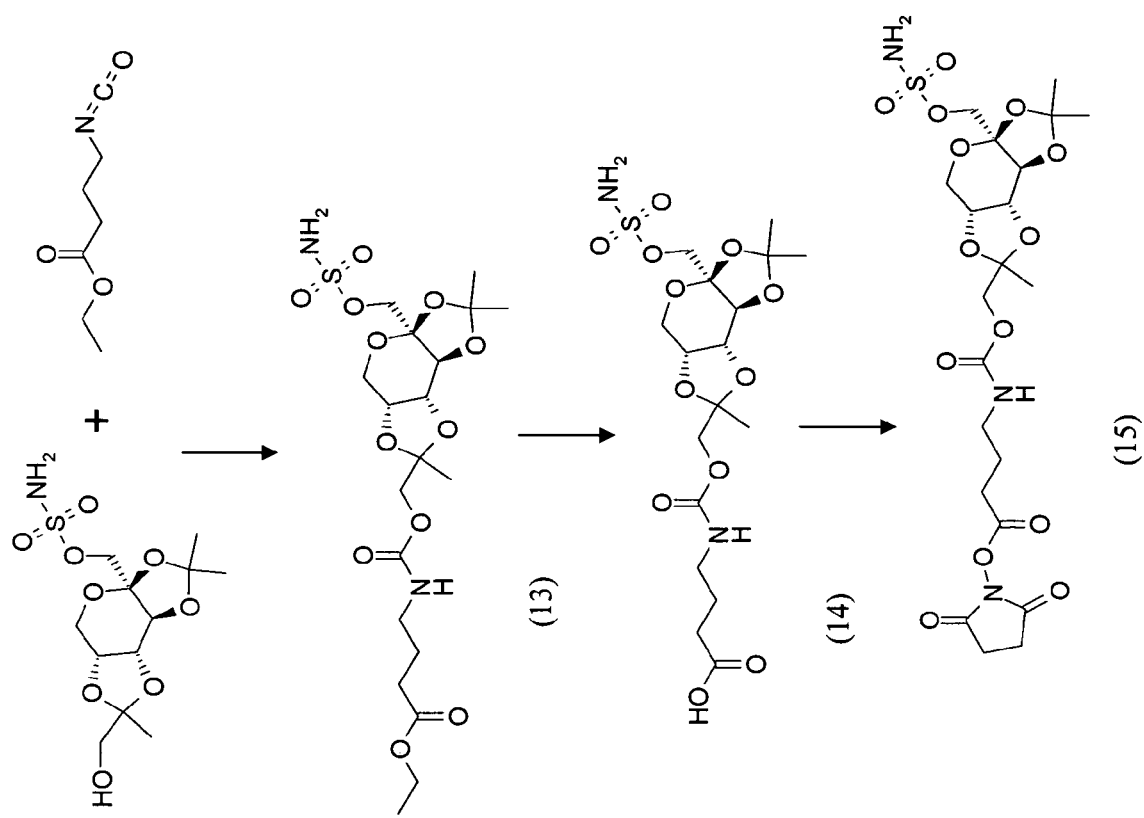
FIG. 14 is a schematic diagram illustrating an embodiment of a synthesis protocol for synthesizing a topiramate analog.

FIG. 14 is a schematic representation of a chemical reaction for converting topiramate into a 9-hydroxy analog of topiramate (13). In a 100 mL round bottom flask a solution of 40 mg of 9-hydroxytopiramate in 10 ml THF (anhydrous) is combined with 0.1 mL N,N-diisopropylethylamine and 0.1 mL ethyl-4-isocyantobutyrate, and stirred under Ar. The reaction mixture is stirred at 80° C. for two days. The reaction is cooled to room temperature and the solvent is removed on a rotary evaporator to produce a residue. The residue is purified by flash column chromatography with an ethyl acetate eluent. The fractions containing the ethyl ester analog of topiramate (13) are combined and concentrated to yield about 20 mg.

Example 13

With continuing reference to FIG. 14, a schematic representation of a chemical reaction is depicted for converting topiramate into a 9 hydroxy analog of topiramate (14). In a 100 mL round bottom flask, a solution of 40 mg of 9-hydroxy topiramate analog (13) in 2 mL methanol is combined with 2 mL aqueous 1N NaOH. The reaction mixture is stirred at room temperature for one day before being concentrated under reduced pressure to produce a residue. The residue is purified by flash column chromatography with an ethyl acetate eluent. The fractions containing the carboxylate analog of topiramate (14) are combined and concentrated to yield about 20 mg.

Example 4

With continuing reference to FIG. 14, a schematic representation of a chemical reaction is depicted for converting carboxylate analog of topiramate (14) into an activated NHS ester of topiramate analog (15). Specifically, a solution of 100 mg of the carboxylate analog of topiramate (11) in 5 mL anhydrous DMF is cooled to 0° C., and 0.1 mL N,N-diisopropylethylamine is added to form a reaction mixture. The reaction mixture is reacted by the addition of 105 mg of O-(N-succinimidyl)-N,N,N',N'-tetramethyluronium tetrafluoroborate. The reaction mixture is allowed to warm up to room temperature and stirred overnight. The reaction mixture is concentrated under reduced pressure, and the residue is purified by flash column chromatography using ethyl acetate/methanol as eluent to give approximately 500 mg of active ester of the topiramate analog (15).

Example 15

Figure 15:
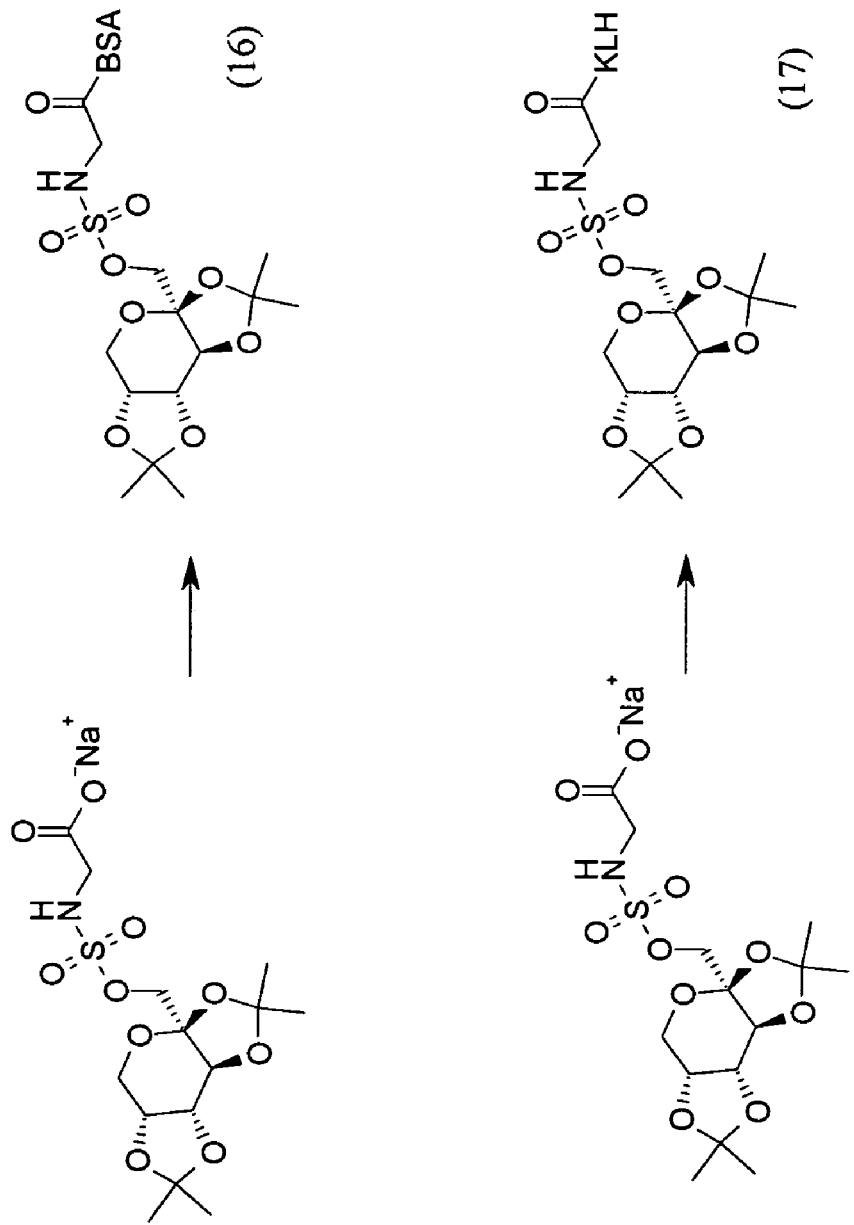
FIG. 15 is a schematic diagram illustrating an embodiment of a synthesis protocol for synthesizing a topiramate analog.

FIG. 15 is a schematic representation of a chemical reaction for converting a topiramate analog into a topiramate antigen (16) for exemplary purposes. The topiramate antigen (16) is based on the U.S. Pat. No. 5,952,182. A solution of 109 mg of N-carboxymethyl-topiramate and 40 mg N-hydroxysuccinimide (NHS) in 2 mL dimethylacetatmide and 0.2 mL N, N-diisopropylethylamine is chilled on a dry ice/isopropanol bath (−20° C. through −15° C.) and treated with 100 µl of 3.15 M dicyclohexycarbodiimide (240 mg DCC in dimethylacetamide) to form a reaction mixture. The reaction mixture is stirred while chilled in the dry ice bath for 15 mm before another 100 µl of DCC solution is added. The reaction mixture is stirred over night under Ar and allowed to warm up to room temperature In a round bottom flask with a magnetic stirrer, about 4 mL pH 7.2 0.1 M PBS buffer having about 70 mg of BSA protein is stirred while being chilled in an ice bath. The protein solution is stirred for 30 min, and 1 mL DMSO is added drop-wise. The foregoing chilled protein solution is added to the topiramate reaction mixture drop-wise, and allowed to be stirred overnight in a cold room (4° C.). The resulting conjugate is placed in a dialysis tube (10,000 MW cut-off) and sequentially dialyzed in 1 L of 20% DMSO in pH 7.2 PBS, then 1 L of 10% DMSO in pH 7.2 PBS, then 1 L of 10% DMSO in pH 7.2 PBS at room temperature, and then followed by four changes with pH 7.2 PBS at 4° C. (1 L each for at least 6 hours each). The protein concentration of antigen (16) is determined as approximately 5.0 mg/mL using a Coomassie Blue protein assay (Bio-Rad).

Example 16

FIG. 15 is a schematic representation of a chemical reaction for converting a topiramate analog into a topiramate immunogen (17) for exemplary purposes. The topiramate immunogen (17) is based on the U.S. Pat. No. 5,952,182. A solution of 109 mg of N-carboxymethyl-topiramate and 40 mg N-hydroxysuccinimide (NHS) in 2 mL dimethylacetatmide and 0.2 mL N,N-diisopropylethylamine is chilled on a dry ice/isopropanol bath (−20° C. through −15° C.) and treated with 100 µl of 3.15 M dicyclohexycarbodiimide (240 mg DCC in dimethylacetamide) to form a reaction mixture. The reaction mixture is stirred while chilled in the dry ice bath for 15 min before another 100 µl of DCC solution is added. The reaction mixture is stirred over night under Ar and allowed to warm up to room temperature during the reaction. In a round bottom flask with a magnetic stirrer about 8 mL pH 7.2 0.1 M PBS buffer having about 80 mg of KLH protein is stirred while being chilled in an ice bath. The protein solution is stirred for 30 min, and 1 mL DMSO is added drop-wise. The foregoing chilled protein solution is added the topiramate reaction mixture drop-wise, and allowed to be stirred overnight in a cold room (4° C.). The resulting conjugate is placed in a dialysis tube (10,000 MW cut-off) and sequentially dialyzed in 1 L of 20% DMSO in pH 7.2 PBS, then 1 L of 10% DMSO in pH 7.2 PBS, then 1 L of 10% DMSO in pH 7.2 PBS at room temperature, and then followed by four changes with pH 7.2 PBS at 4° C. (1 L each for at least 6 hours each). The protein concentration of antigen (17) is determined as approximately 1.6 mg/mL using a Coomassie Blue protein assay (Bio-Rad).

Example 17

Figure 16:
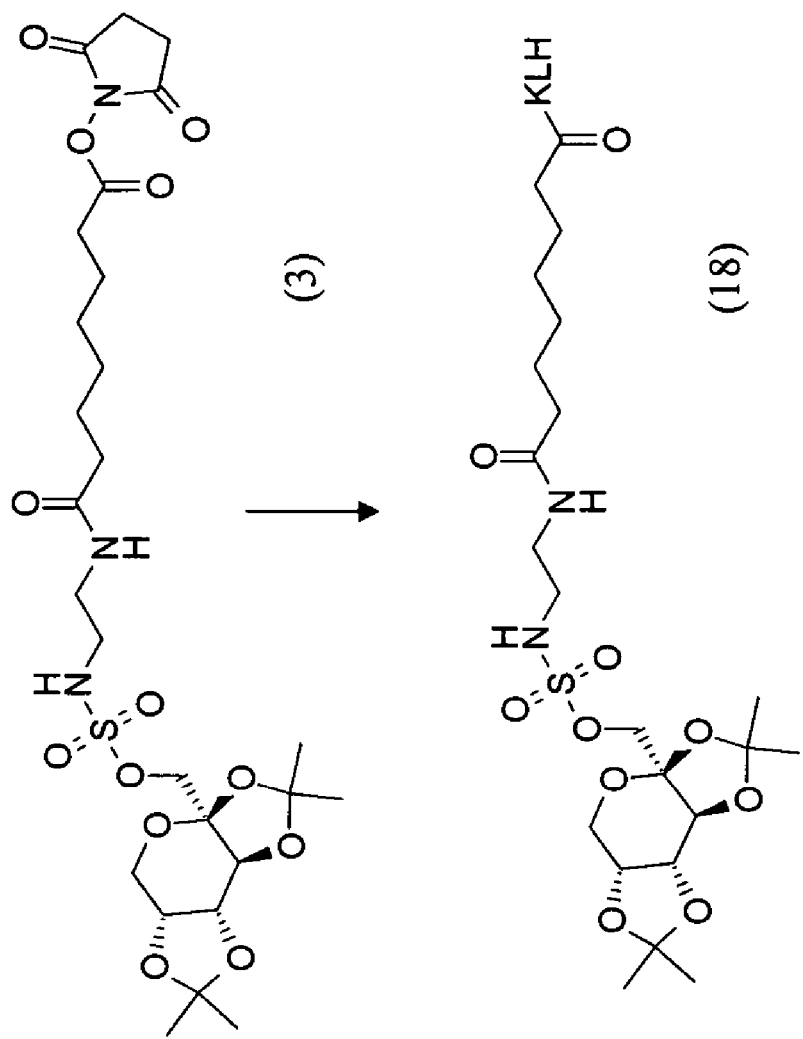
FIG. 16 is a schematic diagram illustrating an embodiment of a synthesis protocol for synthesizing a topiramate analog.

FIG. 16 is a schematic representation of a chemical reaction for converting a topiramate analog (3) into an immunogen (18). A solution of 80 mg of keyhole limpet hemocyanin (KLH) in 8 ml pH 7.2 PBS (0.1 M sodium phosphate, 0.15 M sodium chloride) is cooled in an ice bath. About 5.4 mL of DMSO is added to the KLH solution drop-wise, and maintained below room temperature. A solution of 20.4 mg of topiramate analog (3) in 1.6 mL DMSO is added to the KLH solution drop-wise to form a reaction mixture. The reaction mixture is allowed to stir at room temperature for 40 h. The resulting KLH immunogen (18) is placed in a dialysis tube (10,000 MW cut-off), and serially dialyzed in 1 L of 35% DMSO in pH 7.2 PBS, then 1 L of 10% DMSO in pH 7.2 PBS, then 1 L of 10% DMSO in pH 7.2 PBS at room temperature, and then followed by four changes with pH 7.2 PBS at 4° C. (1 L each for at least 6 hours each). The protein concentration of the KLH immunogen (18) is determined as approximately 2.19 mg/ml using a Coomassie Blue protein assay (Bio-Rad).

Example 18

Figure 17:
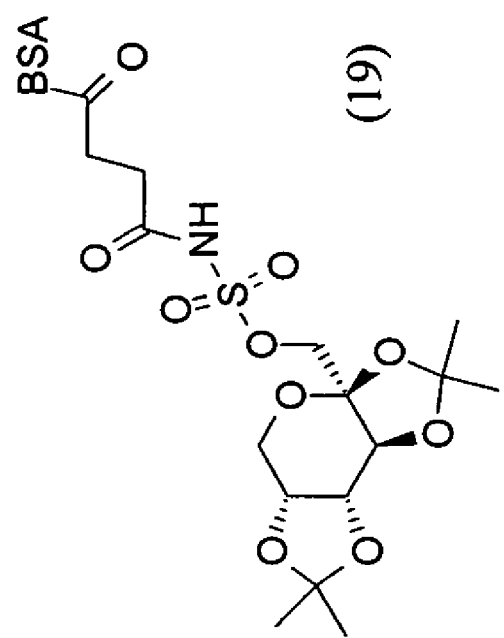
FIG. 17 is a schematic diagram illustrating an embodiment of a synthesis protocol for synthesizing a topiramate analog.
Figure 17:
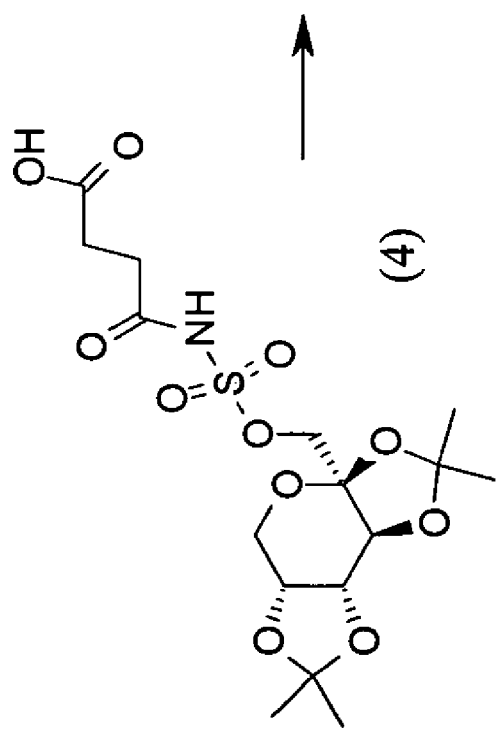

FIG. 17 is a schematic representation of a chemical reaction for converting a succinyl or glutaryl topiramate analog (4) into antigen (19). About 500 mg BSA is placed in a 250 mL round bottom flask and combined with about 37.5 mL PBS. The mixture is stirred in an ice bath for one hour, and a solution of 12.5 ml DMSO is added drop-wise to the BSA solution over a 10 min interval. The resulting solution is stirred in an ice bath for an additional 3 hours. In another round bottom flask, about 170 mg of the succinyl topiramate analog (4) is combined with 2 mL DMF and 0.15 mL N,N-diisopropylethylamine, and stirred in an ice bath under Ar for 20 min. About 130 mg of O, N-succinimidyl, N,N,N,N-tetramethyluronium tetrafluroborate is added to the topiramate analog solution, and then stopped with a rubber septum and stirred at 4° C. for 4 hours. The topiramate analog mixture is added to the above BSA solution drop-wise over 20 min. The resulting topiramate antigen is placed in a dialysis tube (10,000 MW cut-off) and serially dialyzed in 1 L of 30% DMSO in pH 7.2 PBS, then 1 L of 10% DMSO in pH 7.2 PBS, then 1 L of 10% DMSO in pH 7.2 PBS at room temperature, and then followed by four changes with pH 7.2 PBS at 4° C. (1 L each for at least 6 hours each). The protein concentration of the topiramate antigen (19) is determined as approximately 5.0 mg/mL using a Coomassie Blue protein assay (Bio-Rad).

Example 19

Figure 18:
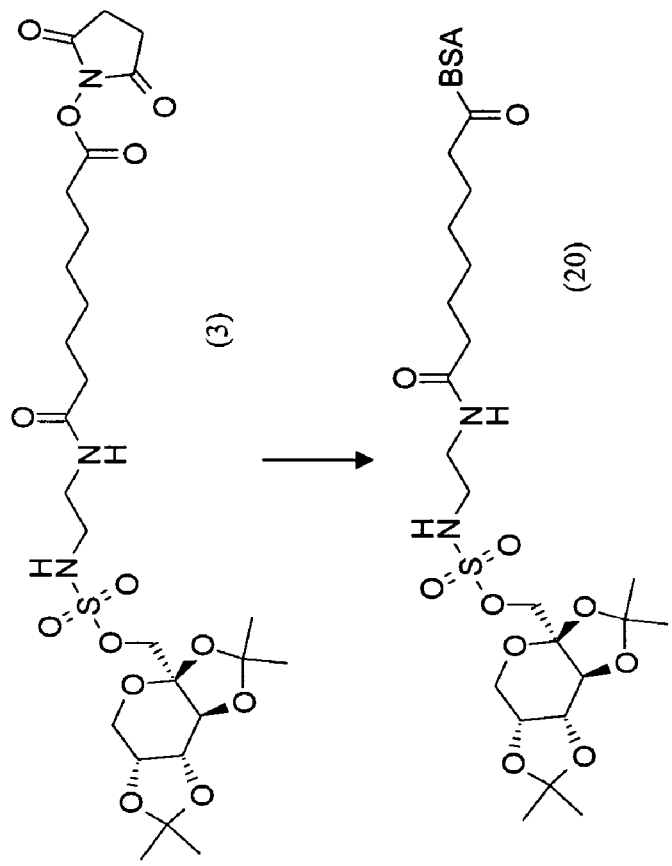
FIG. 18 is a schematic diagram illustrating an embodiment of a synthesis protocol for synthesizing a topiramate analog.

FIG. 18 is a schematic representation of a chemical reaction for converting a succinyl topiramate analog (3) into an antigen (20). A solution of 80 mg of BSA in 4 mL pH 7.2 PBS (0.1 M sodium phosphate, 0.15 M sodium chloride) is cooled in an ice bath. About 5.4 mL of DMSO is added to the BSA solution drop-wise, and maintained below room temperature. A solution of 20.4 mg of topiramate analog (3) in 1.6 mL DMSO is added to the BSA solution drop-wise to form a reaction mixture. The reaction mixture is allowed to stir at room temperature for 40 h. The resulting BSA conjugate (20) is placed in a dialysis tube (10,000 MW cut-off), and serially dialyzed in 1 L of 35% DMSO in pH 7.2 PBS, then 1 L of 10% DMSO in pH 7.2 PBS, then 1 L of 10% DMSO in pH 7.2 PBS at room temperature, and then followed by four changes with pH 7.2 PBS at 4° C. (1 L each for at least 6 hours each). The protein concentration of the BSA conjugate (20) is determined as approximately 5 mg/ml using a Coomassie Blue protein assay (Bio-Rad).

Example 20

Figure 19:
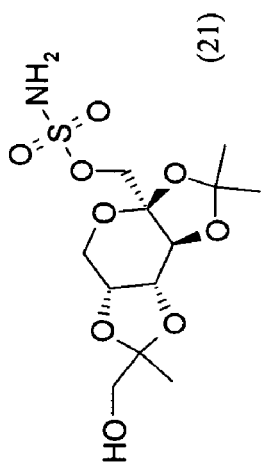
FIG. 19 is a schematic diagram illustrating a topiramate metabolite.

A polyclonal antibody-containing composition is obtained and an assay is performed in order to determine the amount of cross-reactivity of the polyclonal antibody with topiramate and a primary topiramate metabolite. A known amount of topiramate is used to react with an anti-topiramate antibody. A known concentration of topiramate is used to calculate the amount of cross-reactivity between the antibody preparation and the hydroxy metabolite (21) as shown in FIG. 19. The percent of cross-reactivity equals 100 times the observed concentration of topiramate in µg/mL, which is then divided by the concentration of added metabolites in µg/mL. No cross-reactivity is observed in specimens containing those metabolites.

Example 21

A polyclonal antibody that binds with topiramate is prepared using a topiramate analog having an immunogenic conjugate. More particularly, the topiramate immunogens (17) and (18) having the KLH immunogenic moiety are used to generate the anti-topiramate polyclonal antibody. An immunogenic composition is prepared by mixing about 0.5 mL of an immunogen (17) or (18) containing composition with about 0.5 ml. of Freund's adjuvant. The resulting 1 mL immunogenic cocktail is then injected into an animal, such as a sheep or a rabbit. Subsequent immunogenic injections having the same cocktail are administered to the animal every four weeks in order to cause the animal to produce anti-topiramate polyclonal antibody. Sera from animals are screened via ELISA using the same antigens, as described below. Additionally, the polyclonal antibody program can be implemented with topiramate antigens (16), (19), (20) and the like.

Example 22

ELISA plates for use in an ELISA assay are prepared in order to study the polyclonal antibody prepared as described in Example 21. As such, various topiramate antigens (16), (19), and (20) are coated on different ELISA plates before being subjected to the anti-topiramate antibody and competing free topiramate. More particularly, the topiramate antigens are diluted in coating buffer, and then added to the wells of ELISA plate. After the ELISA plate is incubated for 60 min at 37° C., the solvent in the coating buffer is decanted and a blocking buffer is added to the plate. The plate is incubated again for 60 min at 37° C., and the solvent in the blocking buffer is decanted from the plate. The ELISA plate is then stored with the blocking agent in the wells at 2-8° C. for up to 1 week.

Example 23

The antibody titer for a polyclonal antibody prepared in accordance with Example 21 with immunogen (17) is determined using ELISA plates as prepared in Example 22. As such, a serial dilution is performed to produced the same 100 µL volume in each well. The antibody dilutions are prepared between 1:10 and 1:2000 in PBS at pH 7.4 and containing 0.1% BSA. The samples are diluted 10 fold, and the dilutions are started at 1:100 and serially diluted 10 fold across the plate. Subsequently, 100 µL of an antibody sample is added to each well on the ELISA plate. The plate is then incubated for 60 min at 37° C., and washed three times with 250 µL of PBS at pH 7.4 with 0.05% tween. Next, 125 µL of a diluted second antigen (in PBS, pH 7.4), which is different from the antigen previous coated onto the plate, is added to each well of the plate. Titer is determined experimentally by incubating the plate for 60 min at 37° C., which is then washed three times with 250 µL of PBS at pH 7.4 with 0.05% tween. After washing, about 125 µL of ABTS substrate is added to each well in the plates, and the plate is incubated again for 20 min. The plate is read at 405 nm, and the titer results are provided in Table 1.

TABLE 1

| Sheep No. | Immunogen | ELISA Titer | | |
| --- | --- | --- | --- | --- |
| | | Antigen 16 | Antigen 19 | Antigen 20 |
| 5481 | 17 | 210,000 | 85,000 | 130,000 |
| 5492 | 17 | 230,000 | 44,000 | 83,000 |

These results indicate that the antibody titer produced with the immunogen (17) is not sufficient for a microparticle agglutination immunoassay. This is because the microparticles agglutination immunoassay should be conducted with a much higher titer. As such, the immunogen (17) does not produce sufficient antibodies for use in some commercial immunodiagnostic assay protocols.

Example 24

The avidity of the anti-topiramate antibodies prepared with immunogen (17) for topiramate analogs are determined by a binding inhibition study. As such, samples are prepared in 1 mL of PBS at pH 7.4 with 0.1% BSA. A composition having 30% Bmax titer or 50% Bmax titer is used to divide the obtained titer value into approximately half the titer value. Using 30% Bmax, an antibody titer of 1:10000 is diluted to 1:5000 during the sample preparation stage. About 50 µL of topiramate at different concentrations or calibrator values, (0, 2, 4, 8, 16, 32 µg/ml) are then applied to a plate as prepared in accordance with Example 22. About 50 µL of the diluted antibody is dispensed into the plate, and the compositions in the plate are mixed for 1 min on a horizontal plate shaker. The plate is characterized by a first row not containing topiramate or anti-topiramate antibody, wherein the first row is used as a negative control. A second row not containing topiramate is used as the positive control. The plate is incubated for 60 min, and washed three times with 250 μL of PBS at pH 7.4 with 0.05% tween. About 125 μL of a diluted second antibody conjugate such as antigens (16), (19), or (20), in PBS at pH 7.4 is added to each well of the plate. Titer is determined experimentally by the plate being incubated for 60 min at 37° C. and washed 3 times with 250 μL PBS, pH 7.4 with 0.05% tween. Subsequently, about 125 μL of ABTS substrate is added to each well of the plate and incubated for 20 min. The plate is read at 405 nm, and the results are provided in Tables 2 and 3.

TABLE 2

Rabbit No. 5481

| Topiramate (μg/ml) | Antigen 16 | | Antigen 19 | | Antigen 20 | |
|---|---|---|---|---|---|---|
| | Abs | B/Bo | Abs | B/Bo | Abs | B/Bo |
| 0 | 0.76 | 1.00 | 0.83 | 1.00 | 0.60 | 1.00 |
| 2 | 0.29 | 0.38 | 0.33 | 0.40 | 0.32 | 0.53 |
| 4 | 0.26 | 0.34 | 0.25 | 0.30 | 0.30 | 0.50 |
| 8 | 0.18 | 0.24 | 0.20 | 0.24 | 0.25 | 0.42 |
| 16 | 0.15 | 0.20 | 0.18 | 0.22 | 0.22 | 0.37 |
| 32 | 0.11 | 0.14 | 0.15 | 0.18 | 0.18 | 0.30 |

TABLE 3

Rabbit No. 5492

| Topiramate (μg/ml) | Antigen 16 | | Antigen 19 | | Antigen 20 | |
|---|---|---|---|---|---|---|
| | Abs | B/Bo | Abs | B/Bo | Abs | B/Bo |
| 0 | 0.45 | 1.00 | 0.83 | 1.00 | 0.7 | 1.00 |
| 2 | 0.25 | 0.56 | 0.31 | 0.38 | 0.45 | 0.64 |
| 4 | 0.20 | 0.44 | 0.23 | 0.28 | 0.41 | 0.59 |
| 8 | 0.15 | 0.33 | 0.19 | 0.23 | 0.38 | 0.54 |
| 16 | 0.13 | 0.29 | 0.17 | 0.20 | 0.38 | 0.54 |
| 32 | 0.01 | 0.02 | 0.15 | 0.18 | 0.28 | 0.40 |

The inhibition (B/Bo) profiles in Tables 2 and 3 show that the anti-topiramate antibody that is generated with immunogen (17). The immunogen (17) is also used in a commercial FPIA immunoassay to show incremental changes in percent inhibition over the assay range.

Example 25

The antibody titer for a polyclonal antibody prepared in accordance with Example 21 with immunogen (18) is determined using ELISA plates as prepared in Example 22. The titer is determined using an experimental protocol substantially similar with Example 23. The plate is read at 405 nm, and the results are provided in Table 4.

TABLE 4

| | | ELISA Titer | | |
|---|---|---|---|---|
| Sheep No. | Immunogen | Antigen 16 | Antigen 19 | Antigen 20 |
| 5490 | 18 | 320,000 | 210,000 | 980,000 |
| 5495 | 18 | 320,000 | 170,000 | 1,200,000 |

The optimal performance of immunodiagnostic assays can be achieved with high titer (require less antibody, more economical) and good absorbance. Higher titers are especially important in a microparticle agglutination immunoassay. Immunogen (18) is more immunogenic than immunogen (17) due to a longer linker that provides a more accessible epitope. The results from Table 4 indicate that the antibody titer produced with the immunogen (18) is sufficient for use in a commercial topiramate immunodiagnostic assay, such as in a microparticle agglutination immunoassay.

Example 26

The avidity of the anti-topiramate antibodies prepared with immunogen (18) for topiramate analogs is determined by a binding inhibition study performed with an experimental protocol substantially similar as in Example 24. The plate is read at 405 nm, and the results are provided in Tables 5 and 6.

TABLE 5

Rabbit No. 5490

| Topiramate (μg/ml) | Antigen 16 | | Antigen 19 | | Antigen 20 | |
|---|---|---|---|---|---|---|
| | Abs | B/Bo | Abs | B/Bo | Abs | B/Bo |
| 0 | 0.72 | 1.00 | 0.55 | 1.00 | 0.4 | 1.00 |
| 2 | 0.25 | 0.35 | 0.10 | 0.18 | 0.25 | 0.63 |
| 4 | 0.20 | 0.28 | 0.06 | 0.10 | 0.24 | 0.60 |
| 8 | 0.15 | 0.21 | 0.04 | 0.07 | 0.22 | 0.55 |
| 16 | 0.12 | 0.17 | 0.03 | 0.06 | 0.21 | 0.53 |
| 32 | 0.10 | 0.14 | 0.02 | 0.04 | 0.20 | 0.50 |

TABLE 6

Rabbit No. 5495

| Topiramate (μg/ml) | Antigen 16 | | Antigen 19 | | Antigen 20 | |
|---|---|---|---|---|---|---|
| | Abs | B/Bo | Abs | B/Bo | Abs | B/Bo |
| 0 | 0.72 | 1.00 | 0.66 | 1.00 | 0.34 | 1.00 |
| 2 | 0.25 | 0.35 | 0.13 | 0.20 | 0.18 | 0.53 |
| 4 | 0.28 | 0.39 | 0.08 | 0.12 | 0.17 | 0.50 |
| 8 | 0.15 | 0.21 | 0.05 | 0.08 | 0.16 | 0.47 |
| 16 | 0.12 | 0.17 | 0.04 | 0.06 | 0.14 | 0.41 |
| 32 | 0.10 | 0.14 | 0.02 | 0.03 | 0.11 | 0.32 |

Tables 5 and 6 show that the inhibition (B/Bo) profiles of anti-topiramate antibody generated with immunogen (18). The changes in B/Bo appear to be incremental over the assay range. Thus, the antibody is suitable for immunoassay.

Example 27

An immunoturbidimetric or QMS® assay, which is a homogeneous particle-enhanced immunoturbidimetric experiment, is performed to test the polyclonal antibodies prepared as in Example 21. The QMS® assay for topiramate is conducted using a liquid, ready-to-use, two-reagent kit, which contains: R1, which is comprised of sheep polyclonal antibodies that bind with topiramate prepared from immunogen (18) at less than <1% in bis-tris buffer with about sodium azide 0.05%; and R2, which is comprised of topiramate-coated microparticles with antigen (22) at less than 0.5% with sodium azide at 0.05%.

Additionally, suitable specimens can be prepared from serum and plasma. Serum can be collected by standard venipuncture techniques and placed into glass or plastic tubes with or without gel barriers. To ensure complete clot formation has taken place prior to centrifugation, some specimens, especially those from patients receiving anticoagulant or thrombolytic therapy, may exhibit increased clotting time. In the instance the specimen is centrifuged before a complete clot forms, the presence of fibrin may cause erroneous results. Accordingly, the serum can be separated from red blood cells as soon after collection as possible. Plasma can also be used with acceptable anticoagulants, such as lithium heparin, sodium heparin, potassium EDTA, and a heparin gel plasma separator. The plasma can be collected by standard venipuncture techniques and placed into glass or plastic tubes. Also, centrifugation is used to ensure the adequate removal of platelets. The plasma can be separated from red blood cells as soon as possible after collection. The specimens that contain particulate matter or red blood cells may give inconsistent results, but can be centrifuged before testing at a recommended 8,000 to 10,000 RCF×10 minutes to produce a suitable specimen.

The assay procedure is initiated by diluting the specimen because the specimens with topiramate can be used to generate results that exceed the highest calibrator value. As such, the specimens may be diluted manually or by using an automated onboard dilution protocol. The assay is based on competition for topiramate-specific antibody binding sites between drug in the sample and drug coated onto a microparticle of topiramate-coated microparticle reagent is rapidly agglutinated in the presence of the anti-topiramate antibody reagent and in the absence of any competing drug in the sample. The rate of absorbance change is measured photometrically, and is directly proportional to the rate of agglutination of the particles. When a sample containing topiramate is added, the agglutination reaction is partially inhibited, slowing down the rate of absorbance change. A concentration-dependent classic agglutination inhibition curve can be obtained, with maximum rate of agglutination at the lowest topiramate concentration (at zero µg/ml) and the lowest agglutination rate at the highest topiramate concentration (32 µg/ml).

The QMS® topiramate assay is initiated after the being calibrated using a full calibration (6-point) procedure. The QMS® is performed as directed in operation manuals in accordance with the average skill of one in the art. The results are shown in Table 7.

TABLE 7

| Polyclonal antibody R1 Topiramate (µg/ml) sample | Rate (Delta Absorbance) Topiramate antigen (19) coated Latex |
|---|---|
| 0 | 193 |
| 2 | 159 |
| 4 | 122 |
| 8 | 60 |
| 16 | 16 |
| 32 | 4 |

The results shown in Table 7 indicate that the topiramate antigen (19) coated latex particles can effectively compete with topiramate for the anti-topiramate antibody. As such, the topiramate antigen (18) can be used in immunoturbidimetric assays, especially when coupled with a latex particle.

Example 28

Linearity can be measured in order to illustrate an ability to provide results that are directly proportional to the concentration of an analyte in the test sample. As such, linearity typically refers to an overall system response, and the linearity of a system can be measured by testing levels of an analyte, which are known by formulation or known relative to each other. When the system results are plotted against these values, the degree to which the plotted curve conforms to a straight line is a measure of a system linearity.

The protocol to demonstrate the linear range of a quantitative measurement procedure is well known in the art. Briefly, the protocol is used to assess linearity, and the samples with a matrix appropriate to the specimens are analyzed. The following samples are prepared: prepare 1 µg/ml topiramate sample by dilution of Cal B (2.0 µg/ml) with Cal A (0 µg/ml); prepare 3 µg/ml topiramate sample by dilution of Cal C (4.0 µg/ml) with Cal B (2.0 µg/ml); prepare 6 µg/ml topiramate sample by dilution of Cal D (8.0 µg/ml) with Cal C (4.0 µg/ml); prepare 11.9 µg/ml topiramate sample by dilution of Cal E (15.9.0 µg/ml) with Cal C (8.0 µg/ml); and prepare 23.5 µg/ml topiramate sample by dilution of Cal F (31.7 µg/ml) with Cal E (15.9 µg/ml).

The data is collected after a sample or a quality control material is assayed, and reported as the average test result, which is called recovery. The percent recovery is calculated based on the following equation:

$$\% \text{ Recovery} = \frac{\text{Mean recovered concentration}}{\text{Expected concentration}} \times 100$$

The samples are assayed randomly during a single run and the percent recovery is provided in Table 8.

TABLE 8

| Theoretical topiramate concentration (µg/ml) | Recovered topiramate concentration (µg/ml) | % recovery |
|---|---|---|
| 1 | 0.94 | 94.0% |
| 2 | 2.04 | 102.0% |
| 3 | 3.06 | 102.0% |
| 4 | 4.05 | 101.3% |
| 6 | 6.03 | 100.5% |
| 8 | 7.82 | 97.8% |
| 11.9 | 11.62 | 97.6% |
| 15.9 | 15.59 | 98.1% |
| 23.5 | 23.14 | 98.5% |
| 31.7 | 30.51 | 96.2% |
| | | Grand Mean Percentile |
| | | 98.8% |

The percent recovery is within (115% to 85%) range. The data supports the performance of sensitive and accuracy needed in commercial immunodiagnostic assays. The linearity of results is graphically depicted in FIG. 20.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for use in an immunodiagnostic assay for detecting the presence of topiramate in a sample, the system comprising:
   an anti-topiramate antibody raised against an antigen, the anti-topiramate antibody including at least one binding domain having affinity, specificity or avidity for at least one topiramate analog and for topiramate, wherein the binding between the antibody and the at least one topiramate analog is at least 50% of at least one of the affinity, the specificity or the avidity of the antibody for topiramate; and the topiramate analog and the antigen having a chemical structure of Formula 1;

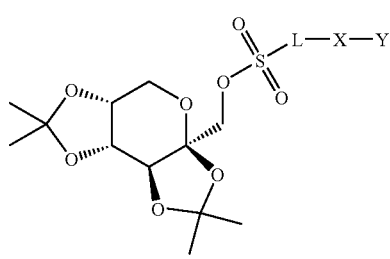

Formula 1 where L is $NH(CH_2)_2NH$;

X is at least one of the group $CH_2$, $(CH_2)_2$, $(CH_2)_3$, $(CH_2)_4$, $(CH_2)_5$, $(CH_2)_6$, $COCH_2$, $CO(CH_2)_2$, $CO(CH_2)_3$, $CO(CH_2)_4$, $CO(CH_2)_5$, $CO(CH_2)_6$, $CO(CH_2)_2CON-HCH_2$, $CO(CH_2)_2CONH(CH_2)_2$, or $CONH(CH_2)_3$; and Y is a chemical moiety selected from the group consisting of COOH, COO—NHS, COO-tertbutyl, OH,; or Y is a $Y_1$-Z where $Y_1$ is selected from the group consisting of at least one of COO, CO, O, CONH, or NH and Z is an operative group.

2. A system as in claim 1, wherein Z is selected from the group consisting of proteins, lipoproteins, glycoproteins, polypeptides, polysaccharides, nucleic acids, polynucleotides, teichoic acids, radioactive isotopes, enzymes, enzyme fragments, enzyme donor fragments, enzyme acceptor fragments, enzyme substrates, enzyme inhibitors, coenzymes, fluorescent moieties, phosphorescent moieties, anti-stokes up-regulating moieties, chemiluminescent moieties, luminescent moieties, dyes, sensitizers, particles, microparticles, magnetic particles, solid supports, liposomes, ligands, receptors, hapten radioactive isotopes, and combinations thereof.

3. A system as in claim 2, wherein the antibody is a polyclonal antibody.

4. A system as in claim 2, wherein the antibody is a monoclonal antibody.

5. A system as in claim 2, further comprising at least one of the following:

a composition comprising an amount of topiramate capable of being diluted into a series of topiramate compositions having a concentration gradient;

a series of compositions containing topiramate at different concentrations, the series of compositions forming a concentration gradient;

the topiramate analog having a tracer moiety;

the topiramate analog having a microparticle;

the antibody coupled to a microparticle;

the topiramate analog having an enzyme donor, and a corresponding enzyme acceptor;

the topiramate analog having an enzyme acceptor, and a corresponding enzyme donor; or the antibody loaded on a particle suitable for separation by filtration or sedimentation; or the antibody at a titer of at least 1:5,000.

6. A system for use in an immunodiagnostic assay for detecting the presence of topiramate in a sample, the system comprising:

an anti-topiramate antibody raised against an antigen, the anti-topiramate antibody including at least one binding domain having affinity, specificity or avidity for at least one topiramate analog and for topiramate, wherein the binding between the antibody and the at least one topiramate analog is at least 50% of at least one of the affinity, the specificity or the avidity of the antibody for topiramate; and the topiramate analog having a chemical structure of Formula 2;

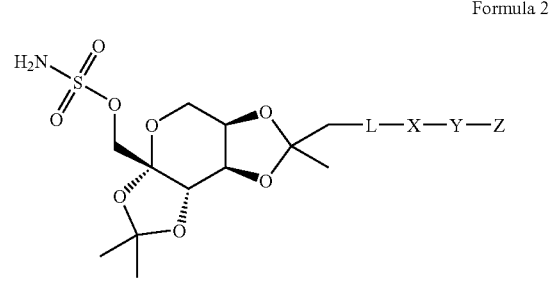

Formula 2 where L is one of the group O;

X is at least one of the group $CH_2$, $(CH_2)_2$, $(CH_2)_3$, $(CH_2)_4$, $(CH_2)_5$, $(CH_2)_6$, $COCH_2$, $CO(CH_2)_2$, $CO(CH_2)_3$, $CO(CH_2)_4$, $CO(CH_2)_5$, $CO(CH_2)_6$, $CO(CH_2)_2CON-HCH_2$, $CO(CH_2)_2CONH(CH_2)_2$, or $CONH(CH_2)_3$; and Y is a chemical moiety selected from the group consisting of COOH, COO—NHS, $COOCH_2CH_3$; or Y is a $Y_1$-Z where $Y_1$ is selected from the group consisting of at least one of COO, CO, O, CONH, or NH and Z is an operative group.

7. A system as in claim 6, wherein Z is selected from the group consisting of proteins, lipoproteins, glycoproteins, polypeptides, polysaceharides, nucleic acids, polynucleotides, teichoic acids, radioactive isotopes, enzymes, enzyme fragments, enzyme donor fragments, enzyme acceptor fragments, enzyme substrates, enzyme inhibitors, coenzymes, fluorescent moieties, phosphorescent moieties, anti-stokes up-regulating moieties, chemiluminescent moieties, luminescent moieties, dyes, sensitizers, particles, microparticles, magnetic particles, solid supports, liposomes, ligands, receptors, hapten radioactive isotopes, and combinations thereof.

8. A system as in claim 7, wherein the antibody is a polyclonal antibody.

9. A system as in claim 7, wherein the antibody is a monoclonal antibody.

10. A system as in claim 7, further comprising at least one of the following:

a composition comprising an amount of topiramate capable of being diluted into a series of topiramate compositions having a concentration gradient;

a series of compositions containing topiramate at different concentrations, the series of compositions forming a concentration gradient;

the topiramate analog having a tracer moiety;

the topiramate analog having a microparticle;

the antibody coupled to a microparticle;

the topiramate analog having an enzyme donor, and a corresponding enzyme acceptor;

the topiramate analog having an enzyme acceptor, and a corresponding enzyme donor; or the antibody loaded on a particle suitable for separation by filtration or sedimentation; or the antibody at a titer of at least 1:5,000.

11. A system as in claim 1, wherein:

L is $NH(CH_2)_2NH$;

X is $CO(CH_2)_6$; and

Y is a linker derived from the chemical moiety, wherein Y is a $Y_1$-Z, with $Y_1$ being CO and Z being an operative group.

12. A system as in claim 1, wherein the antigen has a chemical structure of Formula 3:

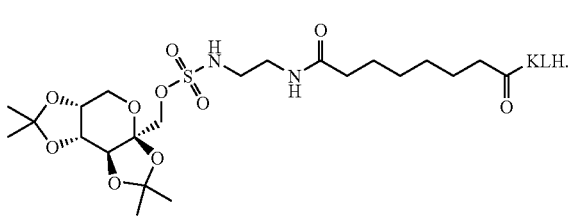

Formula 3

13. A system as in claim 6, wherein:

L is O;

X is $CONH(CH_2)_3$; and

Y is selected from the group consisting of COOH, $COOCH_2CH_3$, and COO-NHS.

14. A system as in claim 6, wherein the antigen has a chemical structure of Formula 3:

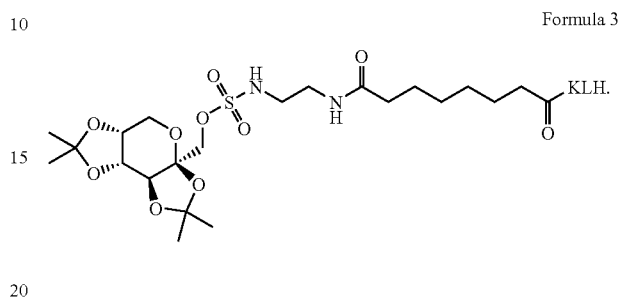

Formula 3

* * * * *

UNITED STATES PATENT AND TRADEMARK OFFICE
CERTIFICATE OF CORRECTION

PATENT NO. : 7,638,291 B2  Page 1 of 4
APPLICATION NO. : 11/254507
DATED : December 29, 2009
INVENTOR(S) : Anlong Ouyang et al.

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 0 days.

Drawings
Sheet 8, Figure 8, Item 528, change "OFCHEMILUMINESCENCE" to --OF CHEMILUMINESCENCE--

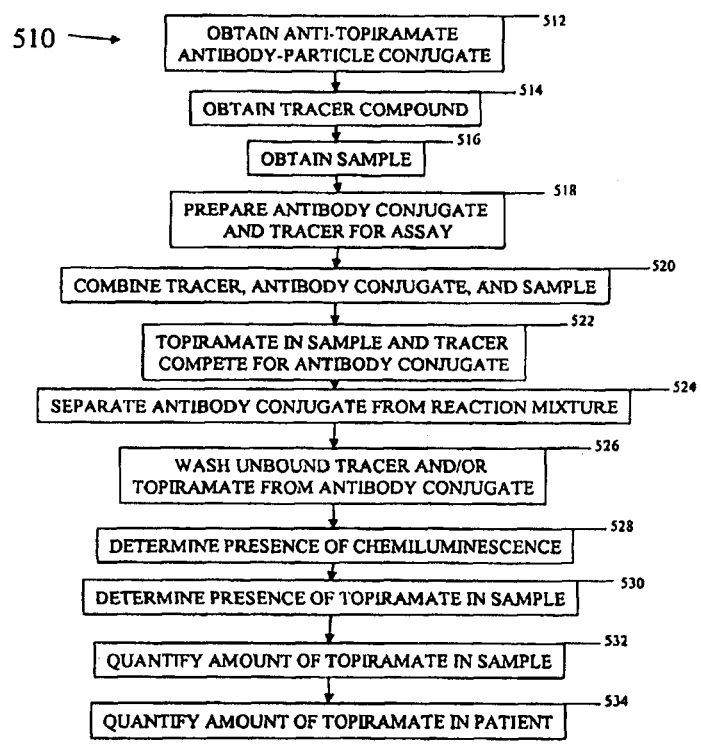

Signed and Sealed this

Third Day of August, 2010

David J. Kappos
*Director of the United States Patent and Trademark Office*

Figure 20:
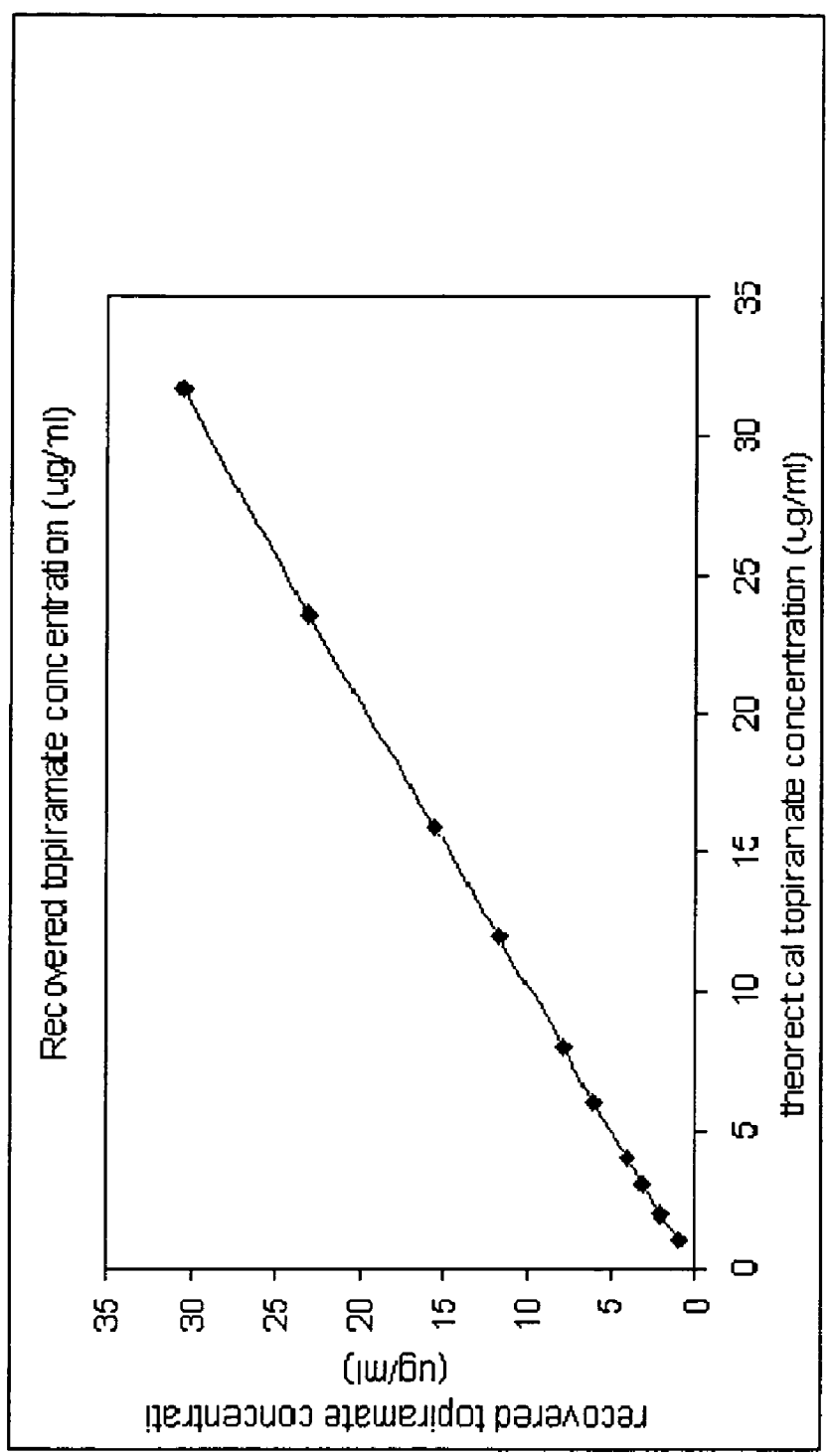
FIG. 20 is graph illustrating topiramate recovery from an embodiment of an agglutination immunoassay.

Sheet 10, Figure 10B, change "DMF" to --THF--
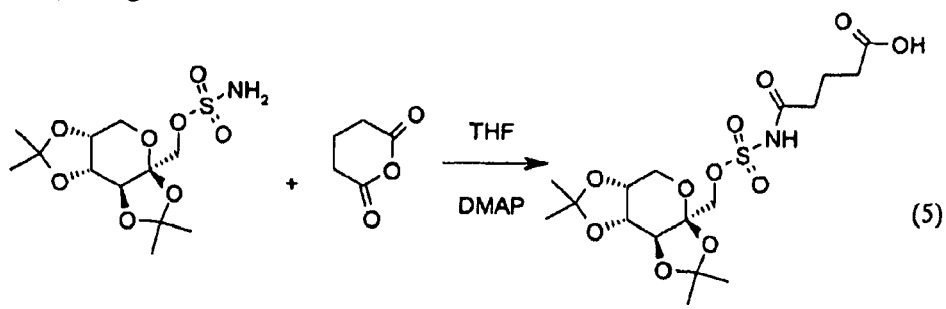
Fig. 10B
Sheet 18, Figure 20, change "Re covered" to --Recovered--
Sheet 18, Figure 20, change "concentrati" to --concentration--
Sheet 18, Figure 20, change "theorectcal" to --theoretical--
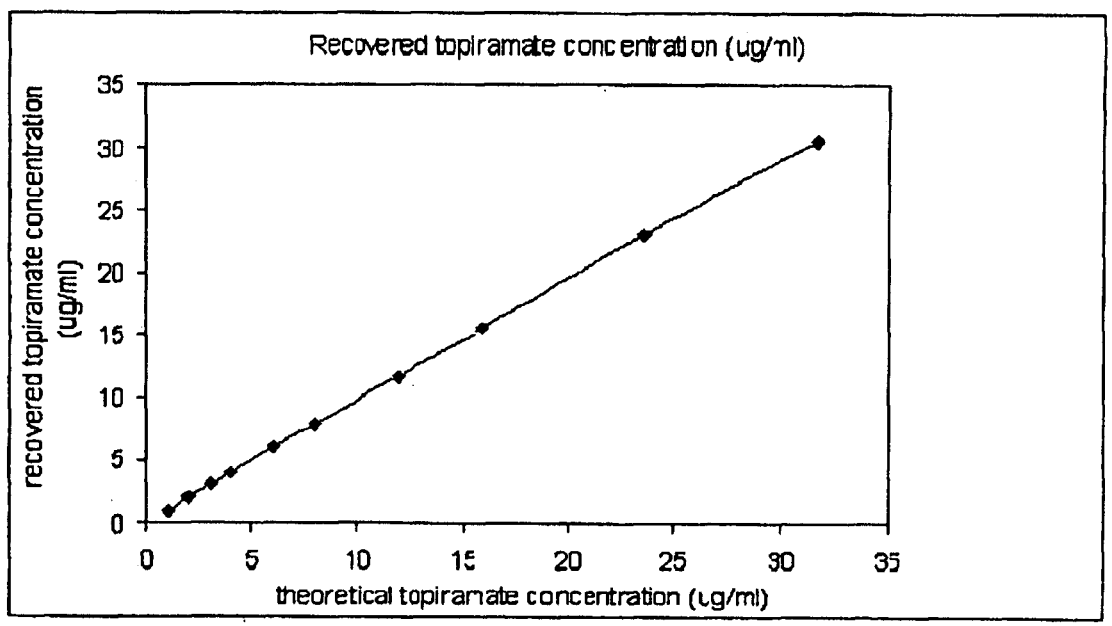
Column 2
Line 18, change "then" to --than--
Line 53, after "but" insert --are--
Column 4
Line 32, before "having" remove [such as a]
Column 7
Line 26, remove [and]

Column 8
Line 36, after "such as" remove [, for example,]
Line 61, after "BSA is" insert --a--

Column 9
Line 55, change "ON-Off" to --On-Off--

Column 10
Line 20, after "assessment" remove [for determining]
Line 30, after "can be" remove [the]
Line 51, change "a experimental" to --an experimental--

Column 11
Line 16, after "surface of" insert --the--

Column 12
Line 5, change "maybe" to --may be--
Line 67, after "such as" remove [, for example,]

Column 13
Line 8, before "molecule" insert --a--
Line 8, after "molecule" remove [is one]
Line 32, change "ethylcylohexylamine" to --ethylcyclohexylamine--

Column 16
Line 49, change "consiting" to --consisting--
Line 49, after "of" remove [is]

Column 17
Line 10, change "binding" to --bonding--

Column 18
Line 55, after "as" remove [,]
Line 55, after "hemocyanin" remove [,]

Column 21
Line 19, before "sample" insert --the--

Column 23
Line 23, change "An anti-topiramate anti-body, such as monoclonal or polyclonal," to --A monoclonal or polyclonal anti-topiramate antibody--

Column 25
Line 22, after "can be" insert --done--

Column 26
Line 26, change "RULE" to --RLUs--

Column 29
Line 34, after "mixture" insert --is--

Column 31
Line 35, change "dimethylacetatmide" to --dimethylacetamide--
Line 40, change "mm" to --min--
Line 42, change "over night" to --overnight--
Line 43, after "temperature" insert --.--
Line 66, change "dimethylacetatmide" to --dimethylacetamide--

Column 32
Line 12, after "added" insert --to--

Column 33
Line 50, after "containing" insert --a--

Column 34
Line 17, change "produced" to --produce--

Column 35
Line 42, after "show" remove [that]

Column 36
Line 44, after "show" remove [that]
Line 58, before "sodium" remove [about]
Line 59, after "azide" insert --at--

Column 37
Line 23, change "between drug in the sample and drug" to --between the drug in the sample and the drug--
Line 24, after "reagent" insert --which--
Line 37, before "being" remove [the]

Column 38
Line 48, change "sensitive" to --sensitivity--

Column 39
Line 1, before "at least" remove [the]

Column 40
Line 5, before "at least" remove [the]
Formula 2, remove [—Z]